United States Patent
Mai et al.

(10) Patent No.: US 9,585,837 B2
(45) Date of Patent: Mar. 7, 2017

(54) THERMALLY STABLE OIL-IN-WATER EMULSIONS CONTAINING AN OIL THAT CONTAINS POLYUNSATURATED FATTY ACIDS

(75) Inventors: Jimbin Mai, Columbia, MD (US); Micah Hazzy Needham, Winchester, KY (US); Gang Su, Ellicott City, MD (US); Wei Wang-Nolan, Ellicott City, MD (US); Chia-Ping Charles Hsu, Ellicott City, MD (US)

(73) Assignee: DSM IP ASSETS B.V., Heerlen (NL)

( * ) Notice: Subject to any disclaimer, the term of this patent is extended or adjusted under 35 U.S.C. 154(b) by 481 days.

(21) Appl. No.: 13/640,106

(22) PCT Filed: Apr. 6, 2011

(86) PCT No.: PCT/US2011/031410
§ 371 (c)(1),
(2), (4) Date: Dec. 22, 2012

(87) PCT Pub. No.: WO2011/127163
PCT Pub. Date: Oct. 13, 2011

(65) Prior Publication Data
US 2013/0210916 A1    Aug. 15, 2013

Related U.S. Application Data

(60) Provisional application No. 61/322,747, filed on Apr. 9, 2010, provisional application No. 61/350,410, filed on Jun. 1, 2010.

(51) Int. Cl.
| A61K 9/107 | (2006.01) |
| A61K 31/20 | (2006.01) |
| A61K 9/00 | (2006.01) |
| A61K 9/19 | (2006.01) |

(52) U.S. Cl.
CPC ............ *A61K 9/107* (2013.01); *A61K 9/0095* (2013.01); *A61K 9/19* (2013.01); *A61K 31/20* (2013.01)

(58) Field of Classification Search
CPC ................................ A61K 9/107; A61K 31/20
See application file for complete search history.

(56) References Cited

U.S. PATENT DOCUMENTS

| 4,199,604 | A | 4/1980 | Kahn et al. |
| 5,156,652 | A | 10/1992 | Gregoli et al. |
| 6,426,078 | B1 * | 7/2002 | Bauer et al. ................. 424/401 |
| 6,596,336 | B1 * | 7/2003 | Gimelli et al. ............... 426/589 |
| 2006/0052446 | A1 | 3/2006 | Chilton et al. |
| 2008/0058418 | A1 * | 3/2008 | D'Angelo et al. ........... 514/560 |
| 2008/0254193 | A1 * | 10/2008 | Edelman et al. ............. 426/602 |

FOREIGN PATENT DOCUMENTS

WO    WO0224152 A2 *  3/2002

OTHER PUBLICATIONS

Binks et al. Effects of pH and Salt Concentration on Oil-in-Water Emulsions Stabilized Solely by Nanocomposite Microgel Particles. Langmuir (2006), vol. 22, pp. 2050-2057.*
International Search Report for PCT/US2011/031410, mailed Jun. 16, 2011.

* cited by examiner

Primary Examiner — Wu-Cheng Winston Shen
Assistant Examiner — Taina D Matos Negron
(74) Attorney, Agent, or Firm — Nixon & Vanderhye P.C.

(57) ABSTRACT

The present invention relates to thermally, stable oil-in-water emulsions comprising an oil comprising a polyunsaturated fatty acid, water, an emulsifier, and a water-soluble stabilizer, and processes for preparing the thermally stable oil-in-water emulsions. The thermally stable oil-in-water emulsions remain flowable at a temperature of −40° C., and are free from a variation in particle size after 9 months in storage at a temperature of −40° C. to −15° C.

19 Claims, 2 Drawing Sheets

THERMALLY STABLE OIL-IN-WATER EMULSIONS CONTAINING AN OIL THAT CONTAINS POLYUNSATURATED FATTY ACIDS

This application is the U.S. national phase of International Application No. PCT/US2011/031410 filed 6 Apr. 2011 which designated the U.S. and claims priority to U.S. Provisional Application No. 61/322,747 filed 9 Apr. 2010 and 61/350,410 filed 1 Jun. 2010, the entire contents of each of which are hereby incorporated by reference.

BACKGROUND OF THE INVENTION

Field of the Invention

The present invention is directed to freezable oil-in-water emulsions comprising an oil comprising one or more polyunsaturated fatty acids, and processes for preparing the freezable oil-in-water emulsions.

Background

Polyunsaturated fatty acids ("PUFAs," including long-chain PUFAs "LC-PUFAs") have been shown to enhance cognitive function and maintain cardiovascular health, among other benefits. In particular, omega-3 PUFAs are important dietary components for preventing arteriosclerosis and coronary heart disease, for alleviating inflammatory conditions, and for retarding the growth of tumor cells, and omega-6 PUFAs are important as both structural lipids, and as precursors for, e.g., prostaglandins and leukotrienes. PUFAs are an important element of a healthy diet, but because PUFAs are not synthesized by humans in vivo, these compounds must be ingested. For example, the oils of many plants and animals (e.g., fish, walnuts, lingonberries, hemp, algae and the seeds and/or leaves of several plants such as flax, chia, perilla and purslane) are rich in PUFAs. Many people also choose to ingest PUFAs through dietary supplements and/or PUFA-enhanced food products. As a result, consumer demand for products that containing PUFAs has recently increased, and a wide range of products now contain PUFAs.

Oil-in-water emulsions have been used as a vehicle for PUFAs, both as a precursor for preparing comestibles, and in particular, as a component in formulated beverages, foods, nutraceuticals, and pharmaceuticals. However, PUFAs present in an emulsion can become unstable and degrade (e.g., via oxidation and/or photolytic degradation), and therefore, maintaining the physical and chemical stability of PUFAs in an emulsion is critical. Freezing a PUFA-containing oil-in-water emulsion is an attractive means for reducing the oxidative potential of PUFAs during shipment and/or storage. Unfortunately, freezing can lead to de-emulsification, and require extended periods of time for thawing prior to use.

What is needed is an oil-in-water emulsion that remains flowable and is resistant to de-emulsification and changes in particle size at sub-freezing temperatures (i.e., temperatures less than 0° C.). Furthermore, what is needed is a freezable oil-in-water emulsion that is resistant to oxidative degradation of a PUFA contained therein.

BRIEF SUMMARY OF THE INVENTION

The present invention provides thermally stable oil-in-water emulsions comprising an oil that comprises a polyunsaturated fatty acid (PUFA) oil, water, an emulsifier, and a water-soluble stabilizer selected from: a mixture of sodium chloride and a monosaccharide, a mixture of propylene glycol and a monosaccharide, and glycerol. When the water soluble stabilizer is selected from a mixture of sodium chloride and a monosaccharide, or a mixture of propylene glycol and a monosaccharide, then the stabilizer can be present in a concentration of about 20% to about 50% by weight of the emulsion. When the water soluble stabilizer is glycerol, then the water-soluble stabilizer can be present in a concentration of about 20% to about 55% by weight of the emulsion. In some embodiments, the thermally stable oil-in-water emulsion remains at least partially liquefied at a temperature of about −80° C., and, in some embodiments, −40° C., and preferably is free from a variation in particle size and organoleptic properties after 9 months in storage at a temperature of about −40° C. to about −15° C., or, at a temperature of about −40° C. to about 0° C., or, at a temperature of about −80° C. to about 0° C., or at a temperature of about −80° C. to about −40° C.

In some embodiments, the emulsion has a minimum 12 month shelf life at freezing temperatures, i.e., temperatures at or below 0° C., preferably between −80° C. to 0° C., and even more preferably between about −40° C. to about −15° C., or, −40° C. to 0° C., or at a temperature of about −80° C. to about −40° C.

In some embodiments, the thermally stable oil-in-water emulsion is free from a variation in particle size and organoleptic properties after 10 freeze-thaw cycles.

In some embodiments, the emulsion has a minimum 9 or 12 month shelf life at freezing temperatures, i.e., temperatures at or below 0° C. and also is free from a variation in particle size and organoleptic properties after 10 freeze-thaw cycles. For example, in some embodiments, the emulsions of the invention are free from a variation in particle size and undesired organoleptic properties when stored at temperatures between −40° C. to 0° C., or, at a temperature of about −40° C. to about −15° C., or, and preferably when stored at temperatures between −80° C. to 0° C., or at a temperature of about −80° C. to about −40° C.

In some embodiments, sodium chloride is present in a concentration of about 10% to about 25% by weight of the emulsion and a monosaccharide is present in a concentration of about 3% to about 15% by weight of an emulsion. In some embodiments, propylene glycol is present in a concentration of about 10% to about 30% by weight of the emulsion, and a monosaccharide is present in a concentration of about 10% to about 30% by weight of the emulsion. In some embodiments, glycerol is present in a concentration of about 25% to about 55% by weight of the emulsion, for example, about 46%, about 47%, about 48%, about 49%, about 50%, about 51%, etc.

In some embodiments, a PUFA is selected from: α-linolenic acid, γ-linolenic acid, linoleic acid, conjugated linoleic acid, arachidonic acid, ω-3 docosapentaenoic acid, ω-6 docosapentaenoic acid, ω-3 eicosapentaenoic acid (eicosapentaenoic acid), docosahexaenoic acid, and combinations thereof. In some embodiments, the PUFA is present in a concentration of about 5% to about 40% by weight of the emulsion.

In some embodiments, an emulsifier is selected from gum acacia, a modified gum acacia, a lecithin, an agar, ghatti gum, a modified ghatti gum, a pectin, a carrageenan, a xanthan gum, a modified starch, especially, a modified food starch, a modified alginate, a polyoxyethylene sorbitan, a polyoxyethylene sorbitan ester, a sugar ester, a fatty alcohol, a natural plant product (e.g., quillaja), mono- and/or di-glycerides, proteins, and combinations thereof. In some embodiments, an emulsifier is present in a concentration of about 10% to about 30% by weight of the emulsion.

In some embodiments, water is present in a concentration of about 20% to about 60% by weight of the emulsion. In some embodiments, the emulsion has a pH of about 2 to about 7.

Thus, in one embodiment the present invention is directed to a thermally stable oil-in-water emulsion comprising: an oil comprising a polyunsaturated fatty acid in a concentration of about 5% to about 40% by weight, water in a concentration of about 20% to about 60% by weight, modified gum acacia or a starch, especially a modified starch such as a modified food starch as an emulsifier, and a water-soluble stabilizer that is sodium chloride in a concentration of about 10% to about 25% by weight and a monosaccharide in a concentration of about 3% to about 15% by weight, wherein the thermally stable oil-in-water emulsion remains at least partially liquefied at a temperature of about −40° C., and is free from a variation in particle size after 9 months in storage at a temperature of about −40° C. to about −15° C., or, at a temperature of about −40° C. to about 0° C., or at a temperature of about −80° C. to about 0° C., or at a temperature of about −80° C. to about −40° C.

In another embodiment, the present invention is directed to a thermally stable oil-in-water emulsion comprising: an oil comprising a polyunsaturated fatty acid in a concentration of about 5% to about 40% by weight, water in a concentration of about 20% to about 60% by weight, modified gum acacia or a starch, especially a modified starch such as a modified food starch as an emulsifier, and a water-soluble stabilizer that is propylene glycol in a concentration of about 10% to about 30% by weight and a monosaccharide in a concentration of about 10% to about 30% by weight, wherein the thermally stable oil-in-water emulsion remains at least partially liquefied at a temperature of about −40° C., and is free from a variation in particle size after 9 months in storage at a temperature of about −40° C. to about 0° C., or, at a temperature of about −40° C. to about −15° C., or at a temperature of about −80° C. to about −40° C., or, at a temperature of about −80° C. to about 0° C., or at a temperature of about −80° C. to about −40° C.

In another embodiment, the present invention is directed to a thermally stable oil-in-water emulsion comprising: an oil comprising a polyunsaturated fatty acid in a concentration of about 5% to about 40% by weight, water in a concentration of about 20% to about 60% by weight, modified gum acacia or a starch, especially a modified starch such as a modified food starch as an emulsifier, and a water-soluble stabilizer that is glycerol in a concentration of about 30% to about 40% by weight, wherein the thermally stable oil-in-water emulsion remains at least partially liquefied at a temperature of about −40° C., and is free from a variation in particle size and organoleptic properties after 9 months in storage at a temperature of about −40° C. to about −15° C., or, at a temperature of about −40° C. to about 0° C., or, at a temperature of about −80° C. to about 0° C., or at a temperature of about −80° C. to about −40° C.

In another embodiment, the present invention is directed to a thermally stable oil-in-water emulsion comprising: an oil comprising a polyunsaturated fatty acid in a concentration of about 5% to about 40% by weight, quillaja as an emulsifier, and a water-soluble stabilizer that is glycerol in a concentration of about 20 to about 40% by weight, and other components as desired, wherein the thermally stable oil-in-water emulsion remains at least partially liquefied at a temperature of −40° C., or, at a temperature of about −80° C. to 0° C., or at a temperature of about −80° C. to about −40° C. and is free from a variation in particle size and organoleptic properties after 9 months in storage at a temperature of about −40° C. to about −15° C., or, at a temperature of about −40° C. to about 0° C., or, at a temperature of about −80° C. to 0° C., or at a temperature of about −80° C. to about −40° C.

In some embodiments, an oil-in-water emulsion of the present invention is substantially free of saccharides.

In some embodiments, an emulsion further comprises a taste-masking agent. In some embodiments, an emulsion further comprises a preservative.

In some embodiments, an emulsion of the invention further comprises an antioxidant. Antioxidants suitable for use with the present invention include, but are not limited to, vitamin C, vitamin E, a polyphenol, a phenol derivative, carnosic acid, lipoic acid, taurine, an aromatic carboxylic acid, salts of an aromatic carboxylic acid, amino acids that have anti-oxidant properties, proteins that have anti-oxidant properties, and combinations thereof.

The present invention is also directed to processes for preparing a thermally stable oil-in-water emulsion. In some embodiments, a process comprises:

combining water and an emulsifier to provide an aqueous mixture, adding to the aqueous mixture an oil comprising a polyunsaturated fatty acid while mixing to provide a oil-in-water emulsion, and adding to the oil-in-water emulsion a water-soluble stabilizer selected from: a mixture of sodium chloride and a monosaccharide, a mixture of propylene glycol and a monosaccharide, and glycerol, wherein the water-soluble stabilizer is present in a concentration of about 20% to about 50% by weight of the emulsion to provide a thermally stable oil-in-water emulsion, wherein the thermally stable oil-in-water emulsion remains at least partially liquefied at a temperature of about −40° C., and is free from a variation in particle size after 9 months in storage at a temperature of about −40° C. to about −15° C., or, at a temperature of about −40° C. to about 0° C., or, at a temperature of about −80° C. to 0° C., or at a temperature of about −80° C. to about −40° C.

Further embodiments, features, and advantages of the present inventions, as well as the structure and operation of the various embodiments of the present invention, are described in detail below with reference to the accompanying drawings.

BRIEF DESCRIPTION OF THE FIGURES

The accompanying drawings, which are incorporated herein and form a part of the specification, illustrate one or more embodiments of the present invention and, together with the description, further serve to explain the principles of the invention and to enable a person skilled in the pertinent art to make and use the invention.

Figure 1:
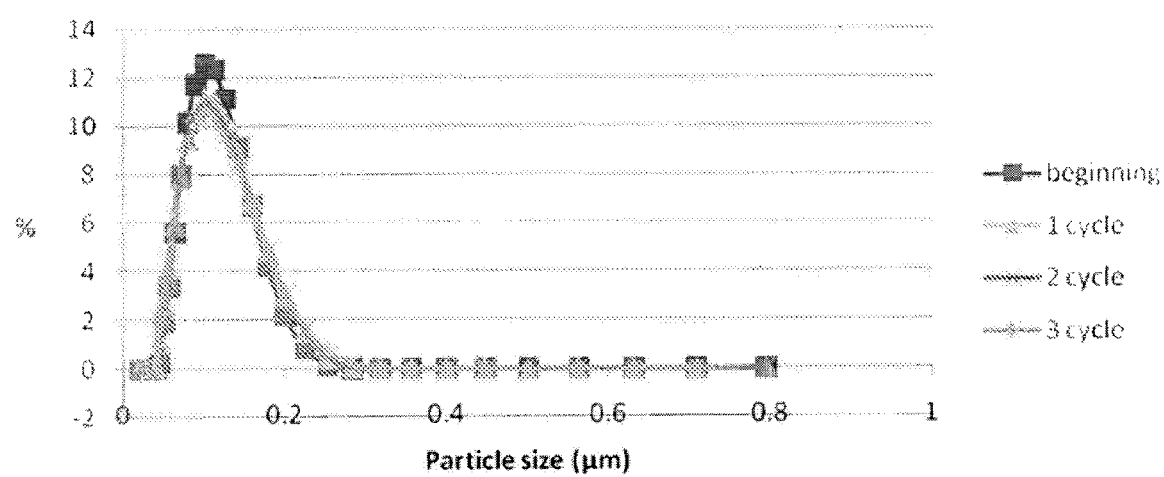
FIG. 1 provides the mean particle size (μm) of the emulsion of Example 4, Table 5, before a freeze/thaw cycle (square), after 1 freeze/thaw cycle (triangle), after 2 freeze/thaw cycles (x), and after three freeze/thaw cycles (star).
Figure 2:
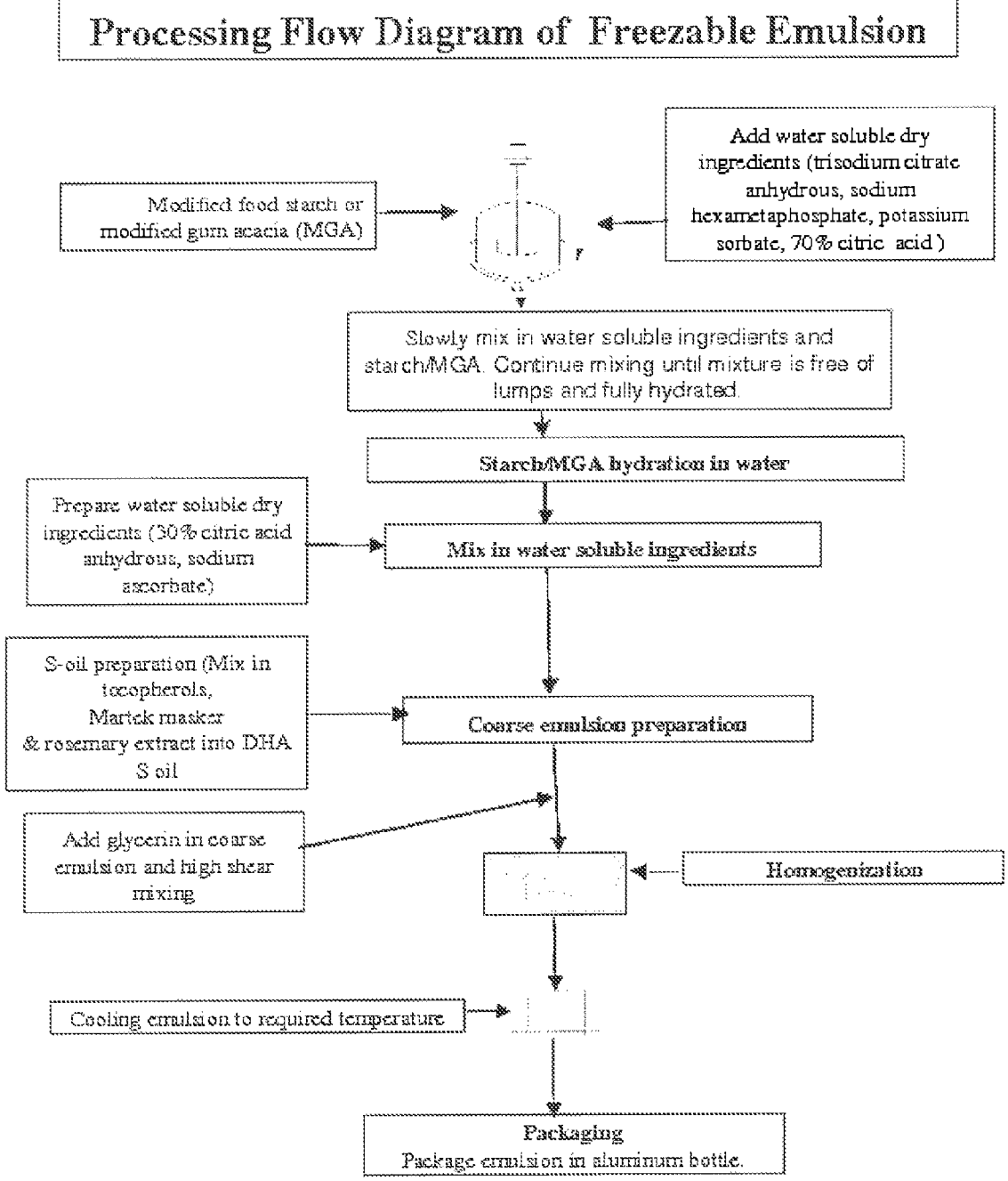
FIG. 2 provides a diagram of the processing for making the thermally stable (freezable) emulsion.

One or more embodiments of the present invention will now be described with reference to the accompanying drawings.

DETAILED DESCRIPTION OF THE INVENTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

Throughout the present disclosure, all expressions of percentage, ratio, incorporation, and the like are "by weight" unless otherwise indicated. As used herein, "by weight" is synonymous with the term "by mass," and indicates that a ratio or percentage defined herein is calculated according to weight rather than volume, or some other measure.

As used herein, "composition" and "mixture" are used interchangeably and refer to a combination of two or more materials, substances, excipients, portions, and the like.

As used herein, "homogeneous" refers to mixtures, compositions, and, in particular, emulsions having a substantially uniform distribution, for example of oil particles in a continuous aqueous phase. Homogeneity is synonymous with uniformity and can refer to intra-sample uniformity, batch-to-batch uniformity, and/or run-to-run uniformity. For example, intra-sample uniformity can be determined by analyzing a first portion of an emulsion, mixture, or composition and comparing this with a second portion of the same emulsion, mixture, or composition. Typical deviations of a composition (e.g., variation in the percentage by weight of excipients, the particle size, and the like) of a substantially homogeneous mixture are about 10% or less, about 5% or less, about 3% or less, about 2% or less, about 1% or less, or within experimental error.

The oil-in-water emulsions of the present invention comprise an immiscible mixture of a continuous aqueous liquid phase and a discontinuous oil phase. As used herein, "continuous aqueous liquid phase" refers to the portion of the emulsion in which the discontinuous oil phase is dispersed. Accordingly, a "discontinuous oil phase" refers to the multiplicity of discrete elements dispersed within, and immiscible with, the continuous aqueous liquid phase. The discontinuous oil phase is present in the form of particles. As used herein, a "particulate" refers to an oil phase of an emulsion that comprises a plurality of discrete particles. As used herein, the term "particle size" refers to particle diameter, which is the diameter of the particles based on an approximate spherical shape of the particle based on a volumetric measurement of the particle. In addition to spherical particles, the oil-in-water emulsions of the present invention can also comprise without limitation semi-spherical, ellipsoidal and/or cylindrical particles.

Assessing whether there has been a change in the particle size distribution of the emulsion over time is a good measure of emulsion stability. A lack of change, or a small change, in particle size distribution of the emulsion over time, indicates the emulsion is stable. As used herein, a particle size "distribution" refers to the number or concentration (e.g., percentage) of particles having a certain size (i.e., diameter), or range of sizes, within a given emulsion, lot and/or batch of the present invention. As used herein, a particle size "distribution" refers to the number or concentration (e.g., percentage) of particles having a certain size (i.e., diameter), or range of sizes, within a given emulsion, lot and/or batch of the present invention. Particle size and particle size distribution can be measured using Low Angle Laser Light Scattering (LALLS) with, for example, a Mastersizer Hydro 2000S (Malvern Instruments Ltd., Worcestershire, UK). Particle size and particle size distribution can also be measured by, for example, micro-photography, video microscopy, video-enhanced microscopy, Coulter counting, differential scanning calorimetry, turbidimetry, dynamic and/or static light scattering, low-intensity ultrasound, nuclear magnetic resonance, or any other particle size measurement technique known to persons of ordinary skill in the art.

As used herein, a "$D_{50}$" or "d(0.5)" value refers to the particle size of an oil phase, and specifically the diameter at which 50% of the measurable particles of the oil phase particles have a larger equivalent diameter, and the other 50% of the particles have a smaller equivalent diameter. Thus, $D_{50}$ generally refers to the median particle diameter.

In some embodiments, the discontinuous oil-phase particles have an average (median) particle size of about 20 nm to about 1.5 µm, about 50 nm to about 1 µm, about 100 nm to about 1.5 µm, preferably about 100 nm to about 1 µm, about 150 nm to about 700 nm, or about 200 nm to 500 nm.

As used herein, a "$D_{90}$" or "d(0.9)" value refers to the particle size of an oil phase, and specifically the diameter at which 90% of all measurable particles of the oil phase have a diameter equal to or less than the $D_{90}$ value, and 10% of the measurable particles have a diameter greater than the $D_{90}$ value.

In some embodiments, the discontinuous oil-phase particles have a $D_{90}$ of about 10 µm or less, about 5 µm or less, about 2 µm or less, or about 1 µm or less.

As used herein, a "$D_{10}$" or "d(0.1)" value refers to the particle size of an oil phase, and specifically the diameter at which 10% of all measurable particles of the oil phase have a diameter equal to or less than the $D_{10}$ value, and 90% of the measurable particles have a diameter greater than the $D_{10}$ value.

In some embodiments, the discontinuous oil-phase particles have a $D_{10}$ of about 50 nm or less, about 60 nm or less, about 70 nm or less, about 80 nm or less, about 90 nm or less, about 100 nm or less, about 200 nm or less, about 250 nm or less, about 300 nm or less, about 400 nm or less, or about 500 nm or less.

As used herein, a "$D_{100}$" or "d(1.000)" value refers to the particle size of an oil phase, and specifically the diameter at which 100% of all measurable particles of the oil phase have a diameter equal to or less than the $D_{100}$ value, and 0% of the measurable particles have a diameter greater than the $D_{100}$ value.

The distribution of particle sizes in a mixture can also be defined by the ratio $D_{10}:D_{50}$, the ratio $D_{10}:D_{90}$, and the ratio $D_{50}:D_{90}$. In some embodiments, the particle size distribution of an oil-in-water emulsion of the present invention is such that the distribution in the emulsion has a ratio of $D_{10}:D_{50}$ of about 1:10 or less, about 1:8 or less, about 1:6 or less, about 1:5 or less, or about 1:3 or less. In some embodiments, the distribution of particle sizes in a mixture, or emulsion, can also be defined by the range of particles that are between about 0.1 µm and about 0.36 µm in diameter. In some embodiments, the percentage of particles that fall within a range of about 0.01 µm to about 0.36 µm in diameter is greater than about 95%, greater than about 96%, greater than about 97%, greater than about 98%, greater than about 99%, or 100% of the particles.

In some embodiments, it is preferred that at least 90% of the particles have a particle size between about 0.02 to about 0.36 microns.

As used herein, a "substantial variation in particle size" refers to an increase in any of $D_{10}$, $D_{50}$ and/or $D_{90}$ of about 10% or more, for example about 20% or more, about 25% or more, about 30% or more, or about 40% or more. In some embodiments, an oil-in-water emulsion of the present invention can be stored for a period of 9 months or more, or 1 year or more, without a substantial variation in particle size.

As used herein, "D[3,2]" refers to the particle size of an oil phase, and specifically the surface weighted mean diameter.

As used herein, "D[4,3]" refers to the particle size of an oil phase, and specifically the volume weighted mean diameter.

As used herein, "emulsion stability" refers to the ability of an emulsion to resist changes in the physical and chemical properties of the emulsion, including physical destabilization such as creaming, flocculation, coalescence, partial coalescence, phase inversion and Ostwald ripening over time and the chemical changes of the emulsion formulation to protect and stabilize a PUFA from, e.g., oxidation. Changes in physical instability are reflected in a change of one or more physical properties of the emulsion, and can include, for example, a change in the pH, viscosity, particle size and/or distribution.

As used herein, "uniformity" refers to absolute deviations from the median.

As used herein, unless otherwise stated or apparent from the context, the terms "or less" or "less than about" refers to percentages that include 0%, or amounts not detectable by current means.

The thermally stable oil-in-water emulsions of the present invention comprise an oil comprising one or more polyunsaturated fatty acids (PUFAs), water, an emulsifier, and a water-soluble stabilizer selected from: (1) a mixture of sodium chloride and a monosaccharide; (2) a mixture of propylene glycol and a monosaccharide, and (3) glycerol. When the water soluble stabilizer is selected from a mixture of sodium chloride and a monosaccharide, or a mixture of propylene glycol and a monosaccharide, then the stabilizer can be present in a concentration of about 20% to about 50% by weight of the emulsion. When the water soluble stabilizer is glycerol, then the water-soluble stabilizer can be present in a concentration of about 20% to about 55% by weight of the emulsion. The thermally stable oil-in-water emulsion remains at least partially liquefied at a temperature of about −40° C., and preferably is free from a variation in particle size and organoleptic properties after 9 months in storage at a temperature of about −40° C. to about −15° C., or, at a temperature of about −40° C. to about 0° C., or, at a temperature of about −80° C. to 0° C., or at a temperature of about −80° C. to about −40° C.

The thermally stable oil-in-water emulsions of the present invention are particularly advantageous because the emulsions can be stored at a temperature below 0° C. for an extended period of time (e.g., 6 months or more, 9 months or more, or 1 year or more) without undergoing a substantial change in particle size or organoleptic quality.

For example, in some embodiments an oil-in-water emulsion of the present invention is free from a variation in particle size when stored at about −40° C. to about −15° C. for a period of 9 months or more, or, at a temperature of about −40° C. to about 0° C., or, at a temperature of about −80° C. to about 0° C., or at a temperature of about −80° C. to about −40° C., for a period of 9 months or more. As used herein, a "variation in particle size" can refer to an increase in any of $D_{10}$, $D_{50}$ and/or $D_{90}$ of about 40% or more, about 30% or more, about 25% or more, about 20% or more, or about 10% or more. Alternatively, a "variation in particle size" can also refer to a decrease in the percentage of particles that are larger than a particular size range. In some embodiments, the decrease in the percentage of particles that fall within a particular size range is to less than 95%. In some embodiments, the particular size range is about 0.01 to about 0.36 μm. In some embodiments, an oil-in-water emulsion of the present invention can be stored for a period of 9 months or more or 1 year or more without a variation in particle size or particle size distribution.

In some embodiments, the thermally stable oil-in-water emulsions are substantially free from coalescence, partial coalescence, flocculation, Ostwald ripening, creaming, sedimentation, de-emulsification, phase inversion, changes in particle size, and/or changes to organoleptic properties and the like, after six months or longer at a temperature of about −40° C. to about −15° C., or, at a temperature of about −40° C. to about 0° C., or, at a temperature of about −80° C. to 0° C., or at a temperature of about −80° C. to about −40° C.

The thermally stable oil-in-water emulsions of the present invention are "freezable" and can be formulated to resist freezing even at −40° C., or, in some embodiments, at a temperature of about −80° C. As used herein, when referring to the oil-in-water emulsions of the present invention as being "freezable," it is intended that the oil-in-water emulsions remain in a flowable, non-solid state at a temperature below the freezing point of water—for example, at temperatures as low as about −41° C. In some embodiments the emulsion remains flowable between about −40° C. to about −15° C., at a temperature of about −40° C. to about 0° C., or, between −80° C. to 0° C., or at temperatures between −80° C. to −40° C.

In some embodiments, the oil-in-water emulsions remain in a flowable, non-solid state at freezing temperatures, for example, of about between −80° C. to 0° C., and preferably at temperatures between −80° C., −75° C., −70° C., −65° C., −60° C., −55° C., −50° C., −45° C., −40° C., −35° C., −30° C., −25° C., −20° C., −15° C., −10° C., −5° C., 0° C., 5° C., 10° C., or 15° C. The thermally stable oil-in-water emulsions of the present invention are fluids, that is they remain fluidic, at temperatures at which refrigerated or ambient emulsions might freeze, for example, about −17° C. to about −21° C. Thus, they are user friendly as they can be used in many applications without thawing before use. For example, the oil-in-water emulsions can be removed from frozen storage (i.e., storage at a temperature at which water would normally freeze), i.e., about −40° C., for example, and used immediately without thawing (or liquefying) the oil-in-water emulsions. If desired, the temperature of the emulsion can be raised to room temperature or higher for use after removal from frozen storage.

As used herein, the term "flowable" refers to the ability of a composition to be transported by gravity or by conventional mechanical or pneumatic pumping means from a storage vessel. Thus, from an ease-of-use and cost-of-ownership standpoint, the thermally stable oil-in-water emulsions of the present invention provide a significant advantage over emulsions that solidify at temperatures at or below 0° C.

As used herein, a "freeze-thaw cycle" refers to a process by which an oil-in-water emulsion is cooled to a temperature of about −40° C. to 0° C. (or at a different temperature if so stated), held at this temperature for at least 24 hours, and then returned to ambient temperature (e.g., 4° C. to 25° C.). In some embodiments, the thermally stable oil-in-water emulsions of the present invention is free from a variation in particle size for at least five or six freeze-thaw cycles, and preferably for at least 12 freeze-thaw cycles. In some embodiments, an oil-in-water emulsion of the present invention is free from a variation in particle size after 10 or more, 12 or more, 15 or more, 20 or more, 25 or more, or 30 or more freeze-thaw cycles.

Of particular advantage is that the oil-in-water emulsions of the present invention are substantially liquid at a temperature of about −40° C. to −15° C., or, at a temperature of about −40° C. to about 0° C., or, at a temperature of about −80° C. to 0° C., or at a temperature of about −80° C. to about −40° C. Thus, while some solids may form in an oil-in-water emulsion of the present invention, the oil-in-water emulsion remains in a non-solid state even when subjected to freezing temperatures, and especially, temperatures as low −40° C., and especially, in some embodiments, of about −80° C.

Not being bound by any particular theory, as an oil-in-water emulsion of the present invention is cooled below 0° C., which is the normal freezing temperature of water, the formation of aqueous solids is inhibited by the presence of a water-soluble stabilizer, which is present in a concentration of 20% to 55% by weight of the emulsion. Thus, the thermally stable oil-in-water emulsions of the present invention remain substantially liquefied at a temperature of −40° C., or, at a temperature of about −80° C.

In some embodiments, the present invention provides a thermally stable oil-in-water emulsion comprising an oil comprising a polyunsaturated fatty acid oil, water, an emulsifier, and a water-soluble stabilizer selected from: a mixture of sodium chloride and a monosaccharide, a mixture of propylene glycol and a monosaccharide, and glycerol. When the water soluble stabilizer is selected from a mixture of sodium chloride and a monosaccharide, or a mixture of propylene glycol and a monosaccharide, then the stabilizer can be present in a concentration of about 20% to about 50% by weight of the emulsion. When the water soluble stabilizer is glycerol, then the water-soluble stabilizer can be present in a concentration of about 20% to about 55% by weight of the emulsion. The thermally stable oil-in-water emulsion remains at least partially liquefied at a temperature of −40° C., and preferably is free from a variation in particle size and organoleptic properties after 9 months in storage at a temperature of −40° C. to −15° C., or, at a temperature of about −40° C. to about 0° C., or, at a temperature of about −80° C. to 0° C., or at a temperature of about −80° C. to about −40° C.

In some embodiments, the emulsion has a minimum 9 month or 12 month shelf life at freezing temperatures, i.e., temperatures at or below 0° C., for example, in some embodiments, the emulsion has a minimum 9 month or 12 month shelf life at −40° C. to −15° C., or, at a temperature of about −40° C. to about 0° C., or, at a temperature of about −80° C. to 0° C., or at a temperature of about −80° C. to about −40° C. In some embodiments, the thermally stable oil-in-water emulsion is free from a variation in particle size and organoleptic properties after 10 freeze-thaw cycles. In some embodiments, the emulsion has a minimum 9 or 12 month shelf life at freezing temperatures, i.e., temperatures at or below 0° C. and also is free from a variation in particle size and organoleptic properties after 10 freeze-thaw cycles.

In some embodiments, sodium chloride is present in a concentration of about 10% to about 25% by weight of the emulsion and a monosaccharide is present in a concentration of about 3% to about 15% by weight of an emulsion. In some embodiments, propylene glycol is present in a concentration of about 10% to about 30% by weight of the emulsion, and a monosaccharide is present in a concentration of about 10% to about 30% by weight of an emulsion. In some embodiments, glycerol is present in a concentration of about 25% to about 55% by weight of the emulsion, for example, about 46%, about 47%, about 48%, about 49%, about 50%, about 51%, etc.

In some embodiments, a PUFA is selected from: α-linolenic acid, γ-linolenic acid, linoleic acid, conjugated linoleic acid, arachidonic acid, ω-3 docosapentaenoic acid, ω-6 docosapentaenoic acid, eicosapentaenoic acid, docosahexaenoic acid, and combinations thereof. In some embodiments, the PUFA is present in a concentration of about 5% to about 40% by weight of the emulsion. In some embodiments, a PUFA is present in the oil-in-water emulsion in an amount of about 50 mg to about 80 mg per gram of emulsion, about 60 mg to about 75 mg per gram of emulsion, or about 65 mg to about 70 mg per gram of emulsion.

In some embodiments, an emulsifier is selected from: a modified gum acacia, a lecithin, an agar, a modified ghatti gum, a pectin, a carrageenan, a xanthan gum, a modified food starch, a modified alginate, a polyoxyethylene sorbitan ester, a sugar ester, and combinations thereof. In some embodiments, an emulsifier is present in a concentration of about 10% to about 30% by weight of the emulsion.

In some embodiments, water is present in a concentration of about 20% to about 60% by weight of the emulsion.

Thus, in one embodiment the present invention is directed to a thermally stable oil-in-water emulsion comprising: an oil comprising a polyunsaturated fatty acid in a concentration of about 5% to about 40% by weight, water in a concentration of about 20% to about 60% by weight, an emulsifier such as, for example, modified gum acacia and/or a starch, especially a modified starch such as a modified food starch, for example, quillaja, and a water-soluble stabilizer that is sodium chloride in a concentration of about 10% to about 25% by weight and a monosaccharide in a concentration of about 3% to about 15% by weight, wherein the thermally stable oil-in-water emulsion remains at least partially liquefied at a temperature of −40° C., and is free from a variation in particle size after 9 months in storage at a temperature of −40° C. to −15° C., or, at a temperature of about −40° C. to about 0° C., or, at a temperature of about −80° C. to 0° C., or, at a temperature of about −80° C. to about −40° C.

In another embodiment, the present invention is directed to a thermally stable oil-in-water emulsion comprising: an oil comprising a polyunsaturated fatty acid in a concentration of about 5% to about 40% by weight, water in a concentration of about 20% to about 60% by weight, an emulsifier such as, for example, modified gum acacia and/or a starch, especially a modified starch such as a modified food starch, for example, quillaja, and a water-soluble stabilizer that is propylene glycol in a concentration of about 10% to about 30% by weight and a monosaccharide in a concentration of about 10% to about 30% by weight, wherein the thermally stable oil-in-water emulsion remains at least partially liquefied at a temperature of −40° C., or, at a temperature of about −80° C. to 0° C., or at a temperature of about −80° C. to about −40° C., and is free from a variation in particle size after 9 months in storage at a temperature of −40° C. to −15° C., or, at a temperature of about −40° C. to about 0° C., or, at a temperature of about −80° C. to 0° C., or at a temperature of about −80° C. to about −40° C.

In another embodiment, the present invention is directed to a thermally stable oil-in-water emulsion comprising: an oil comprising a polyunsaturated fatty acid in a concentration of about 5% to about 40% by weight, water in a concentration of about 20% to about 60% by weight, an emulsifier such as, for example, modified gum acacia and/or a starch, especially a modified starch such as a modified food starch, for example, quillaja, and a water-soluble stabilizer that is glycerol in a concentration of about 30% to about 40% by weight, wherein the thermally stable oil-in-water emulsion remains at least partially liquefied at a temperature of −40° C., and is free from a variation in particle size and organoleptic properties after 9 months in storage at a temperature of −40° C. to −15° C., or, at a temperature of about −40° C. to about 0° C., or, at a temperature of about −80° C. to 0° C., or at a temperature of about −80° C. to about −40° C.

In another embodiment, the present invention is directed to a thermally stable oil-in-water emulsion comprising: an oil comprising a polyunsaturated fatty acid in a concentration of about 5% to about 40% by weight, and a starch, especially a modified starch such as a modified food starch, for example, quillaja as an emulsifier, and a water-soluble stabilizer that is selected from: (1) a mixture of sodium chloride and a monosaccharide; (2) a mixture of propylene glycol and a monosaccharide, and (3) glycerol, such stabilizer being present in a concentration of 29-40% by weight, and other components as desired, wherein the thermally stable oil-in-water emulsion remains at least partially liquefied at a temperature of −40° C., or −80° C., and is free from a variation in particle size and organoleptic properties after 9 months in storage at a temperature of −40° C. to −15° C., or, at a temperature of about −40° C. to about 0° C., or, at a temperature of about −80° C. to 0° C., or at a temperature of about −80° C. to about −40° C.

In another embodiment, the present invention is directed to a thermally stable oil-in-water emulsion comprising: an oil comprising a polyunsaturated fatty acid in a concentration of about 5% to about 20% by weight, about 10 to about 40% of a polymeric hydrocolloid from a plant source, and a water-soluble stabilizer that is glycerol in a concentration of about 5 to about 45% by weight, about 15 to about 50% by weight of water, and other components as desired.

The individual components of the emulsifiers of the claims invention are further described below.

Water Soluble Stabilizer

The thermally stable emulsions of the invention comprises a water-soluble stabilizer selected from: a mixture of sodium chloride and a monosaccharide, a mixture of propylene glycol and a monosaccharide, and glycerol. In addition to preventing solidification of an oil-in-water emulsion of the invention, the water-soluble stabilizer can allow for the formation of smaller oil-phase particles and stabilize the particle size of the discontinuous oil phase through multiple freeze-thaw cycles. In some embodiments, the water-soluble stabilizer can also improve one or more organoleptic properties (e.g., taste, smell, texture, and the like) of the oil-in-water emulsions. In some embodiments, products containing the emulsions of the present invention have good organoleptic qualities compared to products that do not contain the emulsion. In some embodiments, there is either no difference or a very slight/trace difference between products that have the emulsion and products that do have the emulsion.

In some embodiments, the water-soluble stabilizer decreases the viscosity and/or surface tension of the continuous aqueous liquid phase. As a result, the discontinuous oil phase, which includes a PUFA, can be more easily dispersed in the oil-in-water emulsion. In some embodiments, the stability of the oil-in-water emulsions can also be enhanced by minimizing the difference in density between the discontinuous oil phase and continuous aqueous phase.

Water-soluble stabilizers suitable for use with the oil-in-water emulsions of the present invention include a mixture of sodium chloride and a monosaccharide, a mixture of propylene glycol and a monosaccharide, or glycerol.

The total concentration of the water-soluble stabilizer in an oil-in-water emulsion of the present invention is about 20% to about 50%, about 20% to about 40%, about 20% to about 25%, about 35% to about 40%, about 20%, about 25%, about 35%, or about 37% by weight.

In some embodiments, sodium chloride is present in a concentration of about 10% to about 25% by weight of an emulsion. In some embodiments, a monosaccharide is present in a concentration of about % to about 15% by weight of an emulsion. In some embodiments, a monosaccharide is present in a concentration of about 5% to about 10% by weight of an emulsion. In some embodiments, sodium chloride and a monosaccharide are present in a ratio of about 1:1.5 to about 5:1, 1:1 to 4:1, 1:1 to 3:1, 2:1 to 3:1, 1:1, 2:1, 2.5:1, 3:1, or 4:1.

In some embodiments, propylene glycol is present in a concentration of about 10% to about 30% by weight of the emulsion, and a monosaccharide is present in a concentration of about 10% to about 30% by weight of the emulsion. In some embodiments, propylene glycol and a monosaccharide are present in a ratio of about 3:5 to about 5:3, 3:4 to 4:3, or 1:1.

In some embodiments, glycerol (glycerin) is present in a concentration of about 46 to about 55%, about 40 to about 46%, about 25% to about 40%, about 30% to about 40%, about 32% to about 38%, about 34% to about 38%, or about 36% by weight of an emulsion. In some embodiments, glycerol can be present in a concentration greater than about 45%, for example, about 46%, about 47%, about 48%, about 49%, about 50%, about 51%, about 52%, about 53%, about 54% or about 55%. The amount of glycerol can be greater than 45% as above as long as sufficient water is present to hydrate the starch emulsifier so that the starch emulsifier will facilitate encapsulation to a sufficient degree.

Changes in pH of the emulsion over time is a measure of emulsion stability. In a preferred embodiment, the emulsion formulation is well buffered. Such buffering enhances the ability of the emulsion formulation to withstand changes in the process or making and use, changes in its ingredients and other factors.

In some embodiments, an oil-in-water emulsion of the present invention is acidic and in some embodiments it can be a neutral or basic pH. When potassium sulfate is used as a preservative, it is preferable that the oil-in-water emulsion be acidic. The pH of an oil-in-water emulsion can be controlled by the addition of an appropriate amount of an acid and/or a base. Acid and bases suitable for use with the present invention include, but are not limited to, acetic acid, citric acid, hydrochloric acid, sodium hydroxide, sodium carbonate, sodium bicarbonate, and the like. Not being bound by any particular theory, an acidic pH can stabilize the oil-in-water emulsion during storage. In some embodiments, anhydrous citric acid is present in an amount of about 3% to about 8% by weight of an emulsion.

In some embodiments, an oil-in-water emulsion of the present invention has a pH of about 7 or less, about 6 or less, about 5 or less, or about 4 or less. In some embodiments, an oil-in-water emulsion has a pH of about 2 to about 7, about 2.5 to about 6, about 3 to about 5, about 3.5 to about 5, about 4 to about 4.5, or about 4.

Aqueous Liquid Phase

The continuous aqueous liquid phase includes an aqueous liquid, for example a beverage, that is compatible with a PUFA oil, an emulsifier, and a water-soluble stabilizer. Aqueous liquids suitable for use with the continuous aqueous liquid phase include, but are not limited to, water, carbonated water, syrup, diet beverages, carbonated soft drinks, fruit juices (including, but not limited to, white grape, concord dark grape, mixed berry, tropical blends, orange/pineapple/mango, strawberry/banana, pomegranate/ blue berry, white grape/raspberry), vegetable juices, isotonic beverages, non-isotonic beverages, soft drinks containing fruit juice, coffee, tea, dairy products (e.g., milk, cream, and the like), soy products (e.g., milk), and the like, and combinations thereof.

In some embodiments, an aqueous liquid component (e.g., water) is present in a concentration of about 20% to about 75%, about 20% to about 60%, about 25% to about 65%, about 25% to about 60%, about 25% to about 50%, about 25% to about 45%, about 28% to about 35%, about 35% to about 50%, about 40% to about 50%, about 40% to about 45%, about 28%, about 30%, about 35%, about 40%, or about 45% by weight of an emulsion.

In some embodiments, a continuous aqueous liquid phase (i.e., the aqueous liquid and any excipients soluble therein) comprises about 55% to about 95%, about 60% to about 95%, about 70% to about 90%, about 80% to about 90%, about 80% to about 90%, about 80% to about 85%, or about 90% by weight of an oil-in-water emulsion. In some embodiments, a discontinuous oil phase is present in an oil-in-water emulsion of the present invention in a concentration of about 5% to about 45%, about 5% to about 40%, about 10% to about 30%, about 10% to about 20%, about 15% to about 30%, about 15% to about 25%, about 15%, or about 20% by weight of the emulsion.

PUFA Oils

The thermally stable emulsions of the invention comprise a PUFA oil. The thermally stable emulsions of the invention provide an emulsion that can be used to provide a safe and effective administration of a PUFA oil.

The oil-in-water emulsions of the present invention provide safe and effective administration of a PUFA oil. As used herein, a "PUFA" ("PUFA") refers to a fatty acid having a backbone comprising 16 or more carbon atoms, (for example, 16, 18, 20 or 22 carbon atoms ("C16," "C18," "C20," or "C22," respectively)), and two or more carbon-carbon double bonds in the backbone. As used herein, a "long-chain PUFA" ("LC-PUFA") refers to a fatty acid having a backbone comprising 18 or more carbon atoms, and two or more carbon-carbon double bonds in the backbone, for example, C18:3n-3 (alpha-linolenic acid or ALA). When the notation CA:Bn-X is used for a methylene-interrupted PUFA, the "CA" is the number of carbons (for example C18, C20 or C22), B is the number of double bonds and X is the position of the first double bond counted from the methyl end of the fatty acid chain.

As used herein, the term "PUFA" encompasses the free acid form thereof, as well as salts and esters thereof. As used herein, the term "ester" refers to the replacement of the hydrogen in the carboxylic acid group of a PUFA molecule with another substituent. Typical esters are known to those in the art, a discussion of which is provided by Higuchi, T. et al., *Pro-drugs as Novel Delivery Systems*, Vol. 14, A.C.S. Symposium Series, *Bioreversible Carriers in Drug Design*, Ed. Edward B. Roche, Amer. Pharma. Assoc., Pergamon Press (1987), and *Protective Groups in Organic Chemistry*, McOmie ed., Plenum Press, New York (1973), each of which is incorporated herein by reference in the entirety. Examples of common esters include methyl, ethyl, trichloroethyl, propyl, butyl, pentyl, tert-butyl, benzyl, nitrobenzyl, methoxybenzyl and benzhydryl. Other esters of PUFAs are described in U.S. Patent Application Publication No. US 2010-0130608 A1, which is incorporated herein by reference in its entirety.

PUFAs for use with the present invention include omega-3, omega-6, and omega-9 fatty acids, and oxylipins derived therefrom. Exemplary omega-3 PUFAs for use with the present invention include, but are not limited to, α-linolenic acid (C18:3n-3), C18:4n-4, ω-3 eicosapentaenoic acid (20:5n-3) (eicosapentaenoic acid), ω-3 docosapentaenoic acid (docosapentaenoic acid), ω-3 docosahexaenoic acid (22:6n-3), docosatetraenoic acid (22:4n-6), and combinations thereof. Exemplary omega-6 PUFAs for use with the present invention include, but are not limited to, γ-linolenic acid, linoleic acid, conjugated linoleic acid, arachidonic acid (20:4n-6), ω-6 docosapentaenoic acid, and combinations thereof. In some embodiments, a PUFA oil for use with the present invention is all-cis.

In some embodiments, the PUFA comprises DHA. "DHA" refers to docosahexaenoic acid, also known by its chemical name (all-Z)-4,7,10,13,16,19-docosahexaenoic acid, as well as any salts or derivatives thereof. Thus, the term "DHA" encompasses DHA ethyl ester (DHA-EE) as well as DI-IA free fatty acids, phospholipids, other esters, monoglycerides, diglycerides, and triglycerides containing DHA. DHA is an ω-3 polyunsaturated fatty acid.

The term "ester" in the term "DHA-ethyl ester" refers to the replacement of the hydrogen in the carboxylic acid group of the DHA molecule with an ethyl group. In some embodiments, the ester substituent may be added to the DHA free acid molecule when the DHA is in a purified or semi-purified state. Alternatively, the DHA ester is formed upon conversion of a triglyceride to an ester.

In some embodiments, the PUFA oil that is used to make the thermally stable emulsion, is substantially free of one or more specific fatty acids. For example, a PUFA oil that contains DHA-EE can be substantially free of eicosapentaenoic acid (EPA).

EPA refers to eicosapentaenoic acid, known by its chemical name (all-Z)-5,8,11,14,17-eicosapentaenoic acid, as well as any salts or derivatives thereof. Thus, the term "EPA" encompasses the free acid EPA as well as EPA alkyl esters and triglycerides containing EPA. EPA is an ω-3 polyunsaturated fatty acid. Unless otherwise stated, an oil that is used to make the thermally stable emulsion that is "substantially free of EPA" refers to an oil in which EPA is less than about 3%, by weight, of the total fatty acid content of the oil. In some embodiments, the oil that is used to make the thermally stable emulsion comprises less than about 2% EPA, by weight, of the total fatty acid content of the oil, less than about 1% EPA, by weight, of the total fatty acid content of the oil, less than about 0.5% EPA, by weight, of the total fatty acid content of the oil, less than about 0.2% EPA, by weight, of the total fatty acid content of the oil, or less than about 0.01% EPA by weight, of the total fatty acid content of the oil. In some embodiments, the oil has no detectable amount of EPA.

As used herein, an emulsion "substantially free of EPA" can refer to an emulsion in which EPA is less than about 3%, by weight, of the total fatty acid content of the emulsion. In some embodiments, the emulsion comprises, less than about 2% EPA, by weight, of the total fatty acid content of the emulsion, less than about 1% EPA, by weight, of the total fatty acid content of the emulsion, less than about 0.5% EPA, by weight, of the total fatty acid content of the emulsion, less than about 0.2% EPA, by weight, of the total fatty acid content of the emulsion, or less than about 0.01% EPA by weight, of the total fatty acid content of the emulsion. In some embodiments, the emulsion has no detectable amount of EPA.

In some embodiments, the oil or emulsion containing DHA, or especially containing DHA-EE, is substantially free of docosapentaenoic acid 22:5n-6, (DPAn6). The term "DPAn6" refers to docosapentaenoic acid, omega 6, known by its chemical name (all-Z)-4,7,10,13,16-docosapentaenoic acid, as well as any salts or esters thereof. Thus, the term DPAn6 encompasses the free acid DPAn6, as well as DPAn6 ethyl esters and triglycerides containing DPAn6. DPAn6 can be removed during purification of DHA, or alternatively, the DHA can be obtained from an organism that does not produce DPAn6 or produces very little DPAn6.

As used herein, an oil "substantially free of DPAn6" refers to an oil that is used to make the emulsion that contains less than about 2%, by weight, docosapentaenoic acid 22:5n-6, (DPAn6) of the total fatty acid content of the oil. In some embodiments, the oil contains less than about 1% DPAn6, by weight, of the total fatty acid content of the oil. In some embodiments, the oil contains less than about 0.5% DPAn6, by weight, of the total fatty acid content of the oil. In some embodiments, the oil does not contain any detectable amount of DPAn6.

As used herein, an emulsion "substantially free of DPAn6" refers to an emulsion containing less than about 2%, by weight, docosapentaenoic acid 22:5n-6, (DPAn6) of the total fatty acid content of the emulsion. In some embodiments, the emulsion contains less than about 1% DPAn6, by weight, of the total fatty acid content of the emulsion. In some embodiments, the oil contains less than about 0.5% DPAn6, by weight, of the total fatty acid content of the emulsion. In some embodiments, the emulsion does not contain any detectable amount of DPAn6.

The oil or emulsion containing DHA, or especially, containing DHA-EE can also be substantially free of arachidonic acid (ARA). ARA refers to the compound (all-Z) 5,8,11,14-eicosatetraenoic acid (also referred to as (5Z,8Z, 11Z,14Z)-icosa-5,8,11,14-tetraenoic acid), as well as any salts or derivatives thereof. Thus, the term "ARA" encompasses the free acid ARA as well as ARA alkyl esters and triglycerides containing ARA. ARA is an ω-6 polyunsaturated fatty acid. As used herein, an oil used to make the emulsion that is "substantially free of ARA" refers to an oil in which ARA is less than about 3%, by weight of the total fatty acid content of the oil. In some embodiments, the oil comprises, less than about 2% ARA, by weight, of the total fatty acid content of the oil, less than about 1% ARA, by weight, of the total fatty acid content of the oil, less than about 0.5% ARA, by weight, of the total fatty acid content of the oil, less than about 0.2% ARA, by weight, of the total fatty acid content of the oil, or less than about 0.01% ARA, by weight, of the total fatty acid content of the oil. In some embodiments, the oil has no detectable amount of ARA. As used herein, an emulsion "substantially free of ARA" refers to an emulsion in which ARA is less than about 3%, by weight of the total fatty acid content of the emulsion. In some embodiments, the emulsion comprises, less than about 2% ARA, by weight, of the total fatty acid content of the emulsion, less than about 1% ARA, by weight, of the total fatty acid content of the emulsion, less than about 0.5% ARA, by weight, of the total fatty acid content of the emulsion, less than about 0.2% ARA, by weight, of the total fatty acid content of the emulsion, or less than about 0.01% ARA, by weight, of the total fatty acid content of the emulsion. In some embodiments, the emulsion has no detectable amount of ARA.

A PUFA can be added to an emulsion of the present invention as a liquid (e.g., an oil), a solid (e.g., a powder), or a combination thereof.

PUFAs for use with the present invention can be isolated from any PUFA source comprising at least one PUFA capable of being dispersed in an emulsion. A PUFA for use with the present invention can be, for example, from a microbial source, a plant source, a seed source, an animal source, a fish source, or a combination thereof. PUFAs and PUFA sources suitable for use with the present invention include those described in U.S. Patent Application Publication No. 2009-0023808, which is hereby incorporated by reference in its entirety. For example, the PUFAs for use with the present invention can be from an oleaginous microorganism. A PUFA and/or PUFA-containing oil for use with the present invention can also be synthesized.

In some embodiments, a crude PUFA-containing oil (from, e.g., a fish, plant, seed and/or microbial source) is refined (to remove phospholipids and free fatty acids), bleached (to remove any colored bodies), enzyme-treated, and/or winterized (to remove saturated fats).

Commercially available PUFAs suitable for use with the present invention include, but are not limited to, Martek DHA™-S Oil (Martek Biosciences Corp., Columbia, Md.), Rosemary-Free Martek DHA™-S Oil (Martek Biosciences Corp., Columbia, Md.), Microalgae DHA™ Oil (Martek Biosciences Corp., Columbia, Md.), OMEGAPURE® oils (Omega Protein Corp., Houston, Tex.), MARINOL® Oils (Lipid Nutrition, Wormerveer, NL), MEG-3 oils and powders (Ocean Nutrition Corp., Dartmouth, Calif.), Evogel (Symrise AG, Holzminden, Del.), Marine Oil (Arista Industries, Wilton, Conn.), and OMEGASOURCE® oils (Source Food Technology, Inc., Raleigh, N.C.).

In some embodiments, a PUFA oil is present in an oil-in-water emulsion of the present invention in a concentration of about 5% to about 40%, about 10% to about 30%, about 12% to about 25%, about 15% to about 20%, about 12%, about 15%, about 18% or 20% by weight of the emulsion.

In some embodiments, a PUFA oil is present in the discontinuous oil phase of an oil-in-water emulsion of the present invention in a concentration of about 50% to about 99%, about 60% to about 99%, about 70% to about 99%, about 80% to about 99%, about 90% to about 99%, or about 95% to about 99% by weight of the discontinuous oil phase.

In some embodiments, a water-soluble stabilizer and the PUFA are present in a ratio of about 4:1 to about 1:1 by weight, about 3:1 to about 1:1, about 2:1 to about 1:1, about 3:1, about 2:1, about 3:2, or about 1:1 by weight.

Emulsifiers

As used herein, an "emulsifier" refers to a material that promotes the stability of an oil-in-water emulsion such that the discontinuous oil phase remains substantially dispersed within the continuous aqueous liquid phase. Generally, an emulsifier is at least partially soluble in at least the continuous aqueous liquid phase or the discontinuous oil phase. In some embodiments, an emulsifier is partially soluble in both the continuous aqueous liquid phase and the discontinuous oil phase.

Emulsifiers suitable for use in the emulsions of the present invention include any emulsifier compatible with the LC-PUFAs present in the emulsions, including natural, modified, and synthetic emulsifiers, and combinations thereof. Modified emulsifiers include natural emulsifiers that are modified by chemical, enzymatic, and/or physical processes. Emulsifiers particularly suitable for use with the present invention include, but are not limited to, a modified gum acacia (e.g., TICAMULSION®, from TIC Gums, White Marsh, Md.), a lecithin, an agar, a modified ghatti gum, a pectin, a carrageenan, a xanthan gum, a modified starch, especially, a modified food starch, for example, modified corn starch (available from, e.g., National Starch & Chemical, Bridgewater, N.J.), a modified alginate (e.g., esters of alginic acid such as propylene glycol alginate), polyoxyethylene sorbitan, a polyoxyethylene sorbitan ester (e.g., Polysorbate 20, Polysorbate 80, and the like), a sugar ester (e.g., sucrose monostearate, and the like), a fatty alcohol (e.g., cetostearyl alcohol, cetearyl alcohol, cetylstearyl alcohol, and the like), mono- and/or di-glycerides, proteins, and combinations thereof. In some embodiments, the emulsifier can be a polymeric hydrocolloid, especially one that originated from a plant source. Examples of polymeric hydrocolloids that originated from a plant source include plant starches, gum arabic (gum acacia) and lignosulfonates, especially food grade lignosulfonates. In some embodiments, the emulsifier can be a modified gum acacia or a modified starch, such as an acetylated starch or starch octenyl succinate. Examples of a commercially available starch octenyl succinate include Cargill EmulTru™ 12674, which is derived from waxy maize starch. In some embodiments, the emulsifier does not have an HLB value. An "HLB" value refers to the "hydrophilic lipophilic balance" value that is an indication of the degree to which a compound is hydrophilic or lipophilic. In some embodiments, the emulsifier has an HLB value of less than 10. In some embodiments, the oil-in-water emulsion does not contain a polyglycerol fatty acid ester. In some embodiments, the emulsifier can be a natural product, such as a natural product extracted from a plant. Therefore, in some embodiments, the emulsifier is not a polymeric hydrocolloid, but is instead a molecule such as, for example, that provided as quillaja, or Q-Naturale™ (sold by National Starch Food Innovation), which is derived from the quillaja tree, and combinations of emulsifiers such as those listed above.

In some embodiments, the total concentration of emulsifiers present in an oil-in-water emulsion of the present invention is 10% to about 25%, about 10% to about 30%, about 12% to about 20%, about 14% to about 18%, about 14%, about 15%, about 16%, about 20%, or about 25% by weight. In some embodiments, the emulsifier is present in an amount of less than about 10% by weight of the emulsion, for example, when the emulsifier is lecithin.

Excipients

The thermally stable oil-in-water emulsions of the present invention can comprise one or more excipients. As used herein, the term "excipient" refers to the substances useful for combining with a PUFA to provide an oil-in-water emulsion, or to provide one or more desired properties to such emulsion. Excipients suitable for use with the present invention meet all the requirements of the current United States and European Pharmacopeias and various other regulations and standards for pharmaceutical, food, and cosmetic additives. An example of a useful excipient is triacetin (1,2,3-triacetoxypropane; glycerin triacetate). In generally, excipients suitable for use with the present invention are deemed safe for human consumption by the U.S. Food and Drug Administration. As used herein, "safe-for-consumption" refers to excipients, compounds, materials, and/or compositions that are, within the scope of sound judgment, suitable for contact with the tissues of human beings and animals without excessive toxicity, irritation, allergic response, or other possible complications commensurate with a reasonable benefit/risk ratio. In addition, one of skill in the art will recognize that pharmaceutically acceptable excipients can be used in the present invention including those listed in *The Handbook of Pharmaceutical Excipients*, 5th Ed., The Pharmaceutical Press and American Pharmacists Association, London, UK and Washington, D.C. (2006), which is incorporated herein by reference in its entirety.

In some embodiments, a PUFA contained in an oil-in-water emulsion of the present invention is substantially undetectable by taste and/or smell to a consumer. Thus, an emulsion of the present invention can be ingested by a consumer without any undesirable odor and/or taste. In some embodiments, an emulsion further comprises a taste-masking agent, or a flavor-masking agent, suitable for masking a scent and/or taste from an oil-in-water emulsion of the present invention or a product prepared using an oil-in-water emulsion of the present invention. Taste-masking agents suitable for use with the present invention include, but are not limited to, Martek Masker (Martek Biosciences Corp., Columbia, Md.) (supplied by Firmenich (Geneva, Switzerland)) and also known as Firmenich Masker), which is a type of vanilla flavor, Givaudan (Vernier, Switzerland), international Flavors and Fragrances (New York, N.Y.), Sensient Technologies (Milwaukee, Wis.), and Ogawa Flavors and Fragrances (Tokyo, Japan), and combinations thereof. In some embodiments, the taste-masking agent is present in an amount of less than 5%, less than 2%, or less than 1% by weight of an emulsion.

The oil-in-water emulsions of the present invention have an extended shelf life. As used herein, "shelf-life" refers to a time period within which embodiments of emulsions may be stored and remain suitable for consumer use. Thus, in addition to particle size stability, the oil-in-water emulsions of the present invention protect and stabilize a PUPA from, e.g., oxidation. For example, when dosed at 32 mg DHA/250 ml, the emulsions of the present invention remain stable and organoleptically acceptable for 9-12 months in shelf stable dark juice like Concord grape juice.

In some embodiments, an oil-in-water emulsion of the present invention further comprises an antimicrobial agent, such as potassium sorbate, or sodium benzoate, or propylene glycol (if it is not already in the emulsion), or mixtures thereof. Such antimicrobial agents can be included in the composition in amounts up to the maximum allowable amount in food and/or beverage compositions. For example, compositions of the invention can include an antimicrobial agent in an amount of between about 0.05 to about 0.1% by weight of the emulsion.

In some embodiments, an oil-in-water emulsion of the present invention further comprises a preservative. Preservatives suitable for use with the present invention include, but are not limited to, vitamin C, a tocopherol, ascorbic acid or a salt thereof (e.g., potassium sorbate), metal chelators (i.e., metal chelating agent) (e.g., ethylenediaminetetraacetic acid ("EDTA") and salts thereof), sulfite and salts thereof (e.g., sodium sulfite, potassium sulfite, and the like), bisulfite and salts thereof (e.g., sodium bisulfite and the like), cysteine hydrochloride, a polyphosphate (e.g., sodium hexametaphosphate, sodium acid pyrophosphate, mono sodium disodium phosphates and the like), and combinations thereof. In some embodiments, the preservatives are present in an amount of less than 7%, less than 6%, less than 5%, less than 4%, less than 3%, less than 2%, or less than 1%.

In some embodiments, an oil-in-water emulsion of the present invention further comprises one or more antioxidants. As used herein, "antioxidants" refer to compounds that slow or prevent the oxidation of another chemical species, such as vitamins, pigments and lipids. Antioxidants suitable for use with the present invention include, but are not limited to, vitamin C (including fat soluble forms such as ascorbyl palmitate), vitamin E (tocopherols), a polyphenol, a phenol derivative (e.g., butylated hydroxytoluene, butylated hydroxyanisole, tert-butylhydroquinone, and the like), carnosic acid, lipoic acid, taurine, an aromatic carboxylic acid (e.g., cinnamic acid, benzoic acid, ascorbic acid and the like), salts of an aromatic carboxylic acid (e.g., sodium ascorbate, potassium ascorbate, and calcium ascorbate), amino acids that have anti-oxidant properties, proteins that have anti-oxidant properties, and combinations thereof. Ascorbate (ascorbic acid) helps to retard lipid oxidation by reacting with oxygen to eliminate it from food. Ascorbic acid can also help to regenerate oxidized tocopherols to the reduced state so that the tocopherols can continue to function as a free radical scavenger. Thus, the combination of ascorbic acid and tocopherol is especially advantageous and such combination results in a synergistic effect with regard to enhancing the free radical scavenger ability of the tocopherol.

Suitable polyphenol antioxidants can be found in, and extracted from, a variety of foods, including plants (e.g., extracts of rosemary, cumin, grape seeds, pine bark, oats, watercress, basil, ginger, red clover, and the like), tea leaves (e.g., green tea, mate (also known as chimarrão or cimarrón), and the like), fruits (e.g., pomegranate, apple, white cherry, plum, wolfberries, blueberries, tomatoes, papaya, grapes, and the like), vegetables (e.g., alfalfa and the like), and cocoa, or may be synthesized. Exemplary polyphenols include both natural extracts and synthetic compounds. Polyphenols also include, but are not limited to, a flavone (e.g., apigenin, luteolin, tangeritin, chrysin, baicalein, scutellarein, wogonin, diosmin, flavoxate, and the like), a flavonol (e.g., 3-hydroxyflavone, azaleatin, fisetin, galangin, gossypetin, kaempferide, daempferol, isorhamnetin, morin, myricetin, natsudaidain, pachypodol, quercitin, isoquercitin, quercitrin, rhamnazin, rhamnetin, and the like), a flavanol (e.g., (+)-catechin, (-)-epicatechin, (-)-epicatchin gallate, (-)-epigallocatechin, and epigallocatechin gallate), a flavone (e.g., apigenin, luteolin, tangeritin, chrysin, baicalein, scutellarein, wogonin, diosmin, flavoxate, and the like), a flavanone, an isoflavone, a tannin, a stilbene derivative, (e.g., resveratrol and the like), an anthocyanin, an anthocyanidin, a proanthocyanidin, gallic acid, curcumin, and combinations thereof.

An antioxidant can be present in an oil-in-water emulsion of the present invention in a concentration of about 0.01% to about 10%, about 0.02% to about 8%, about 0.05% to about 5%, about 2% to about 20%, about 3% to about 18%, about 4% to about 15%, about 5% to about 12%, about 6% to about 10%, or about 7% to about 9% by weight of an emulsion. In some embodiments, an antioxidant is present in an amount of less than about 10%, less than about 5%, or less than about 2% by weight of the emulsion.

In some embodiments, an oil-in-water emulsion further comprise a flavorant, which can be a synthetic, natural, fruit, or botanical flavorant, or a combination thereof. Flavorants suitable for use with the present invention include, but are not limited to, strawberry, grape, raspberry, cherry, almond, citrus fruit, orange, tangerine, lemon, lime, lemon-lime, vanilla, vanilla cream, cocoa, chocolate, coffee, kola, tea, mint, spearmint, wintergreen, menthol, licorice, butterscotch and combinations thereof.

In some embodiments, an oil-in-water emulsion further comprises a flavor enhancer, which as used herein, refers to an excipient added to achieve a better tasting product or provide a more pleasant mouth feel during administration. Non-limiting examples of flavor enhancers suitable for use with the present invention include ribotide and monosodium glutamate.

In some embodiments, an oil-in-water emulsion further comprises a natural or artificial sweetener. Suitable sweeteners include, but are not limited to, sucrose, lactose, fructose, acesulfame salts (e.g., acesulfame potassium and the like), alitame, aspartame, brazzein, curculin, cyclamic acid and salts thereof (e.g., sodium cyclamate), dihydrochalcones, glycyrrhizin and salts thereof, a mogroside, mabinlin, monatin and salts thereof, monellin, neotame, saccharin and salts thereof (e.g., saccharin sodium), siamenoside, stevia, stevioside, sucralose, thaumatin, and combinations thereof.

In some embodiments, a sweetener is present in an oil-in-water emulsion of the present invention in a concentration of about 0.01% to about 20%, about 0.01% to about 1%, about 0.02% to about 15%, about 0.05% to about 10%, about 5% to about 20%, about 0.1% to about 5%, about 0.5% to about 4%, about 1% to about 3%, about 0.01%, about 0.05%, about 0.1%, about 1%, about 5%, or about 10% by weight of the emulsion.

In some embodiments, an oil-in-water emulsion is "sugar-free" (i.e., substantially free of a sugar and/or complex carbohydrates and/or polysaccharides that can be readily converted to a sugar in the oral cavity.

In some embodiments, an oil-in-water emulsion further comprises a colorant. A "colorant" refers to a substance that can be added to an oil-in-water emulsion to enhance and/or modify color or appearance, such as, for example, anthocyanins and oligomeric procyanidins. A colorant can also be added to an oil-in-water emulsion as a code or identifier (i.e., to indicate the concentration, intended use, and the like). Any type of colorant (i.e., "natural color" and/or "artificial color" such as F.D.&C. dyes) known to be "generally regarded as safe" (GRAS) by the FDA, and thus generally used in the confectionary trade, or otherwise approved by the FDA for use in pharmaceutical and/or nutraceutical preparations, can be used with the present invention.

In some embodiments, the discontinuous oil phase further comprises a material selected from: a terpene (e.g., limonene, pinene, and the like), a flavor oil, a vegetable oil, an essential oil, and the like, and combinations thereof. Essential oils suitable for use with the present invention include, but are not limited to, a citrus oil (e.g., an oil of lemon, orange, lime, grapefruit, mandarin, bitter orange, and the like), a leaf oil (e.g., oil or mint, peppermint, and the like), a spice oil (e.g., oil of bergamot, rosemary, and the like), a seed oil (e.g., flax seed oil, cranberry seed oil, and the like), a peel oil, and combinations thereof.

In some embodiments, an oil-in-water emulsion of the present invention further comprises a weighting agent. Weighting agents suitable for use with the present invention include, but are not limited to, a brominated oil (e.g., brominated vegetable oil), ester gum and other wood rosins, sucrose diacetate hexa-isoburtyurate (SAIB), refined gum dammar, ganuaba wax, benzyl benzoate polyglyceryl ester, glyceryl tribenzoate, and combinations thereof.

In some embodiments, a weighting agent is present in a continuous aqueous liquid phase in a concentration of about 1% to about 30%, about 2% to about 25%, or about 3% to about 20% by weight of the continuous aqueous liquid phase.

In some embodiments, an oil-in-water emulsion of the present invention further comprises a water-dispersible or oil-dispersible bioactive. As used herein, "water dispersible bioactive" refers to materials which are both dispersible and soluble in water (or an aqueous liquid), and "oil dispersible bioactive" refers to materials which are both dispersible and soluble in an oil. Water- and/or oil-dispersible bioactives suitable for use with the present invention include, but are not limited to, an enzyme (e.g., papain), a carotenoid (e.g., β-carotene, lycopene, astaxanthin, zeaxanthin, lutein, and the like, and oxygenated variants thereof), a terpene and/or terpenoid (e.g., eucalyptol, camphor, menthol, citral, and the like), an essential oil (e.g., eugenol, gingerol, avenacoside, and the like), a phenolic acid (e.g., gallic acid, rosmarinic acid, and the like), a flavonoid (e.g., naringin, quercetin, a catechin, an anthocyanin, a coumarin, and the like), a phytoestrogen, a proanthocyanidin, a curcuminoid, a vitamin (e.g., vitamin E, Vitamin K, and the like), and combinations thereof. In some embodiments, a water dispersible bioactive is present in an oil-in-water emulsion in a concentration of about 0% to about 20%, about 0.5% to about 15%, or about 1% to about 10% by weight of the emulsion.

In some embodiments, an oil-in-water emulsion of the present invention further comprises a folded oil. Folded oils suitable for use with the present invention include, but are not limited to, 3-fold, 4-fold, 5-fold, 6-fold, 8-fold, 10-fold, 15-fold, and 20-fold oils of bergamot (including bergaptene-free bergamot oil), grapefruit (including high-aldehyde grapefruit oil and grapefruit juice extracts), lemon, lime, mandarin, orange (as well as orange juice extracts), tangerine, and the like, and combinations thereof. Folded oils suitable for use with the present invention also include washed, distilled, cold pressed, terpene-free, and/or sesquiterpene-free variants of the above exemplary folded oils.

In some embodiments, a folded oil is present in an oil-in-water emulsion of the present invention in a concentration of about 0.1% to about 10%, about 0.2% to about 5%, about 0.3% to about 1%, about 0.5% to about 5%, or about 1% to about 3% by weight of the emulsion.

In some embodiments, an oil-in-water emulsions of the present invention is substantially free from mono- and/or di-glycerides. As used herein, "substantially free from mono- and/or di-glycerides" refers to the oil-in-water emulsions of the present invention comprising about 10% or less, about 5% or less, about 1% or less, about 0.5% or less, about 0.1% or less, about 0.05% or less, or an undetectable concentration of mono- and/or di-glycerides, by weight of the emulsion.

The thermally stable oil-in-water emulsions of the present invention can be used as a component or a functional ingredient in, for example, a food product, a beverage, an herbal composition, a dietary supplement, a nutritional product, a pharmaceutical composition (especially one that is administered orally or by enteral feeding), and/or a nutraceutical composition. The oil-in-water emulsions of the present invention can be present in such compositions in a concentration suitable to provide a health benefit to a consumer upon use (e.g., ingestion) of the product.

Thus, in some embodiments, the method of the present invention comprises administering daily to the subject in need of the same, a thermally stable emulsions of the invention, or a product or composition containing the same, comprising a PUFA, especially DHA, or most especially DHA-EE substantially free of eicosapentaenoic acid (EPA), wherein the DHA is derived from a non-algal source, e.g., fish.

The term "subject" refers to mammals such as humans or primates, such as apes, monkeys, orangutans, baboons, gibbons, and chimpanzees. The term "subject" can also refer to companion animals, e.g., dogs and cats; zoo animals; equids, e.g., horses; food animals, e.g., cows, pigs, and sheep; and disease model animals, e.g., rabbits, mice, and rats. The subject can be a human or non-human. The subject can be of any age. For example, in some embodiments, the subject is a human infant, i.e., post natal to about 1 year old; a human child, i.e., a human between about 1 year old and 12 years old; a pubertal human, i.e., a human between about 12 years old and 18 years old; or an adult human, i.e., a human older than about 18 years old. In some embodiments, the subject is an adult, either male or female.

As used herein, the terms "treat" and "treatment" refer to both therapeutic treatment and prophylactic or preventative measures, wherein the object is to prevent or slow down (lessen) an undesired physiological condition or disease, or obtain beneficial or desired clinical results. The term "treatment" also refers to the alleviation of symptoms associated with the above conditions or diseases.

In some embodiments, the preparation containing the PUFA provided by the emulsion of the invention is administered continuously. The term "continuous" or "consecutive," as used herein in reference to "administration," means that the frequency of administration is at least once daily. Note, however, that the frequency of administration can be greater than once daily and still be "continuous" or "consecutive," e.g., twice or even three or four times daily, as long as the dosage levels as specified herein are achieved.

In some embodiments, an oil-in-water emulsion is a concentrate suitable for dilution by a local formulator, bottler, distributor, pharmacy, or other entities at the point of distribution and/or use. Concentrated oil-in-water emulsions are particularly suitable for products that must be shipped and/or stored prior to use.

As used herein, a "concentrate" refers to an oil-in-water emulsion suitable for dilution to produce a final oil-in-water emulsion having a lower concentration of emulsifier and PUFA. For example, a concentrate can comprise a beverage emulsion concentrate that can be diluted to form a beverage. In particular, the emulsion concentrate is easily dispersed within a continuous aqueous liquid phase, without further homogenization required. The formation of emulsion concentrates allows for the storage of LC-PUFAs in a stable and compact form for storage as well as transport before being dosed into a final emulsion form for consumption by a consumer. In addition, homogenization of the emulsion concentrate may be carried out in a smaller scale than homogenization of a final emulsion form to be consumed by a consumer. Thus, lower equipment costs are realized.

In some embodiments, the concentrate of the present invention can be added to solids or semi-solids. For example, an emulsion concentrate may be added to solid or semi-solid foods or beverages including, but not limited to, mayonnaise, whipped topping, ice cream, yogurt, smoothies, sauces, fruit concentrate, fruit puree, baby food, specialty coffees such as frappes, etc., and teas, especially iced or specialty coffees and teas that contain milk or milk products such as chai tea, Thai ice tea (cha-yen), and the like, and combinations thereof.

In some embodiments, "carry-over" additives, such as potassium sorbate, may be present in the final product, and at a level that is considered to be "non-functional." For example, a carry through level of potassium sorbate of 1-3 ppm when delivering 32 mg DHA in 8 oz of beverage is considered to be "non-functional." For foodstuffs, a carry-over additive is a substance, the presence of which in a given product is due solely to the fact that the additive was contained in one or more ingredients that went into the making of the product and that serve no technological function in the finished product.

Processes for Preparing the Emulsions

The oil-in-water emulsions of the present invention can be prepared using any method suitable for mixing an aqueous liquid phase and a discontinuous oil phase to provide an oil-in-water emulsion. In some embodiments, an emulsifier and a aqueous phase material are mixed slowly to provide a stable dispersion, followed by the addition of an optional antioxidant, an optional preservative, an optional pH-adjusting agent, and the like. This homogenous aqueous phase mixture is then mixed vigorously while slowly adding oil-phase materials (e.g., a PUFA, an optional taste-masking agent, an optional antioxidant, an optional preservative, and the like) to provide an oil-in-water emulsion. Alternatively, an aqueous liquid, an emulsifier, and oil-phase ingredients can be combined simultaneously to form an oil-in-water emulsion.

The water-soluble stabilizer can be added before, during, and/or after formation of the oil-in-water emulsion. In some embodiments, a first portion of the water-soluble stabilizer is added to the aqueous phase mixture prior to emulsification, and a second portion of the water-soluble stabilizer is added to the oil-in-water emulsion after emulsification.

In some embodiments, a substantially aqueous composition is prepared comprising water and an emulsifier, and the pH of the aqueous composition is adjusted as described herein by adding an appropriate amount of an acid and/or a base prior to emulsification.

In processes comprising a sequential addition of ingredients, a substantially homogeneous aqueous phase composition (e.g., a dispersion) is prepared comprising an aqueous liquid, an emulsifier, and one or more optional excipients, and the oil phase ingredients (e.g., a PUFA and one or more optional excipients) are mixed in parallel to provide a substantially homogeneous oil phase mixture. The mixed oil phase ingredients are then slowly added to the aqueous phase composition while vigorously mixing to provide an oil-in-water emulsion.

In some embodiments, an emulsifier is added to both an aqueous phase and an oil phase prior to emulsification.

In some embodiments, an emulsion concentrate comprising a portion of an aqueous liquid, an emulsifier, and a discontinuous oil phase is prepared, and a remaining portion of the aqueous liquid is then added to the emulsion concentrate to form the emulsion.

In some embodiments, a process comprises: combining water and an emulsifier to provide an aqueous mixture, adding to the aqueous mixture a polyunsaturated fatty acid (preferably an oil comprising a polyunsaturated fatty acid) while mixing to provide a oil-in-water emulsion, and adding to the oil-in-water emulsion a water-soluble stabilizer selected from: a mixture of sodium chloride and a monosaccharide, a mixture of propylene glycol and a monosaccharide, and glycerol, wherein the water-soluble stabilizer is present in a concentration of 20% to 50% by weight of the emulsion to provide a thermally stable oil-in-water emulsion, wherein the thermally stable oil-in-water emulsion remains at least partially liquefied at a temperature of −40° C., and is free from a variation in particle size and free from a variation in, or from undesired, organoleptic properties after 9 months in storage at a temperature of −40° C. to −15° C.

In some embodiments, an initially formed oil-in-water emulsion is homogenized by passing the oil-in-water emulsion through a homogenizer one or more times (e.g., once, twice, thrice, or 4 or more times) to form a final oil-in-water emulsion. For example, the emulsion can be passed through a homogenizer at a pressure of 10000 psi total/500 psi second stage, with 5 passes. In another example, the homogenization pressure can be 5000 psi total/750 psi second stage with 2 passes. The pressure and number of passes is determined by the homogenizer scale and type, and the final particle size that is desired.

In some embodiments a scraped surface heat exchanger (SSHE) is used with preparations or materials that have a high viscosity, especially to heat and cool the preparation and for pasteurization, if desired, for example with products that contain potassium sorbate. In some embodiments, a homogenizer is connected to the scraped surface heat exchanger.

In some embodiments, the mixing is performed under nitrogen blanketing.

Having generally described the invention, a further understanding can be obtained by reference to the examples provided herein. These examples are given for purposes of illustration only and are not intended to be limiting.

EXAMPLES

Example 1

An oil-in-water emulsion of the present invention was prepared as follows. Potassium sorbate (750 mg) and sodium ascorbate (40.12 g) were added to water (558.54 g) and dissolved. Modified gum acacia (200.59 g) was added to the water mixture, which was then covered and mixed slowly (200 rpm) for 4-6 hours. Any foam that formed atop the solution was discarded. After slowly mixing, the pH of the water mixture was adjusted to pH 4 by adding an appropriate amount of citric acid. The water mixture was used as a base for an oil-in-water emulsion.

An oil mixture was prepared by combining and mixing Martek algal oil (40% DHA oil) (90 g, Martek Biosciences Corp., Columbia, Md.), rosemary extract (157.5 mg; rosemary STABILENHANCE® OSR 5%, 001280, Naturex Inc.), and flavor masker (900 mg, Flavor Masking 599469AH, Firmenich, also called Martek Masker).

A portion of the water mixture (358.9 g) was placed in a high-shear mixer and mixed at 6,100 rpm while the oil mixture was slowly added to provide an oil-in-water emulsion. Both the water mixture and the oil mixture were at 25° C. during the mixing. The mixing was continued until the entirety of the oil mixture was emulsified.

The emulsion was homogenized using first stage pressure of 15,000 psi and a second stage pressure of 2,000 psi. The emulsion was cycled through the homogenizer for about 30 seconds before collecting a first pass product. After passing through the homogenizer, the emulsion was cooled by passing the product hose through an ice bath, and then collected. The first 10 seconds of product were discarded. The homogenization process was repeated three times to provide the oil-in-water emulsion, which was placed in a high-shear mixer and mixed at 1,500 rpm. Dextrose (27 g) was slowly added to the emulsion, followed by sodium chloride (67.5 g) to provide the final emulsion, which was bottled, nitrogen purged, and kept at a freezing temperature (−17° C. to −21° C.).

TABLE 1

Composition of the final emulsion prepared in Example 1.

| Ingredient | Percent (w/w) |
| --- | --- |
| Water | 44% |
| Martek Algal Oil (40% DHA oil) | 15.8% |
| Modified Gum Acacia[a] | 15.8% |
| NaCl | 15% |
| Dextrose | 6% |
| Sodium Ascorbate | 3.16% |
| Citric Acid Anhydrous | 0.87% |

TABLE 1-continued

Composition of the final emulsion prepared in Example 1.

| Ingredient | Percent (w/w) |
|---|---|
| Flavor Masker[b] | 0.16% |
| Potassium Sorbate | 0.06% |
| Rosemary Extracts[c] | 0.03% |

[a]TICAMULSION ® A-2010 Powder (TIC Gums)
[b]Flavor Masking 599469AH (Firmenich)
[c]Rosemary STABILENHANCE ® OSR 5% 001280 (Naturex Inc.)

Example 2

An oil-in-water emulsion of the present invention was prepared as follows. Potassium sorbate (730 mg) and sodium ascorbate (38.74 g) were added to water (287.55 g) and dissolved. Dextrose (169.49 g) was added to the water mixture and dissolved, heating if needed. The water mixture was then cooled (if needed) and propylene glycol (193.7 g) was added, and the resulting water mixture was mixed well. Modified gum acacia (159.8 g) was then added to the water mixture, which was then covered and mixed slowly (200 rpm) for 4-6 hours. Any foam that formed atop the solution was discarded. After slowly mixing, the pH of the water mixture was adjusted to pH 4 by adding an appropriate amount of citric acid.

A portion of the water mixture (394.9 g) was placed in a high-shear mixer and mixed at 6,100 rpm while the oil mixture was slowly added to provide an oil-in-water emulsion. Both the water mixture and the oil mixture were at 25° C. during the mixing.

The mixing was continued until the entirety of the oil mixture was emulsified. The emulsion was homogenized using front pressure of 15,000 psi and a back pressure of 2,000 psi. The emulsion was cycled through the homogenizer for about 30 seconds before collecting a first pass product. After passing through the homogenizer, the emulsion was cooled by passing the product hose through an ice bath, and then collected. The first 10 seconds of product were discarded. The homogenization process was repeated three times to provide the oil-in-water emulsion, which was bottled, nitrogen purged, and kept at a freezing temperature (−17° C. to −21° C.).

TABLE 2

Composition of the final emulsion prepared in Example 2.

| Ingredient | Percent (w/w) |
|---|---|
| Water | 29.7% |
| Propylene Glycol | 20% |
| Dextrose | 17.5% |
| Modified Gum Acacia[a] | 16.5% |
| Martek Algal Oil (40% DHA oil) | 12% |
| Sodium Ascorbate | 4% |
| Citric Acid Anhydrous | 0.5% |
| Flavor Masker[b] | 0.2% |
| Rosemary Extracts[c] | 0.04% |
| Potassium Sorbate | 0.08% |

[a]TICAMULSION ® A-2010 Powder (TIC Gums)
[b]Flavor Masking 599469AH (Firmenich)
[c]Rosemary STABILENHANCE ® OSR 5% 001280 (Naturex Inc.)

Example 3

An oil-in-water emulsion of the present invention was prepared as follows. Potassium sorbate (730 mg) and sodium ascorbate (38.74 g) were added to water (287.55 g) and dissolved. Modified gum acacia (159.8 g) was then added to the water mixture, which was then covered and mixed slowly (200 rpm) for 4-6 hours. Any foam that formed atop the solution was discarded. After slowly mixing, the pH of the water mixture was adjusted to pH 4 by adding an appropriate amount of citric acid. Glycerol (162 g) was then added to the water mixture and the water mixture was mixed well.

A portion of the water mixture (216.3 g) was placed in a high-shear mixer and mixed at 6,100 rpm while the oil mixture was slowly added to provide an oil-in-water emulsion. Both the water mixture and the oil mixture were at 25° C. during the mixing. The mixing was continued until the entirety of the oil mixture was emulsified.

The emulsion was homogenized using front pressure of 15,000 psi and a back pressure of 2,000 psi. The emulsion was cycled through the homogenizer for about 30 seconds before collecting a first pass product. After passing through the homogenizer, the emulsion was cooled by passing the product hose through an ice bath, and then collected. The first 10 seconds of product were discarded. The homogenization process was repeated three times to provide the oil-in-water emulsion, which was bottled, nitrogen purged, and kept at a freezing temperature (−17° C. to −21° C.).

TABLE 3

Composition of the final emulsion prepared in Example 3.

| Ingredient | Percent (w/w) |
|---|---|
| Glycerin | 36% |
| Water | 28% |
| Martek Algal Oil (40% DHA oil) | 15% |
| Modified Gum Acacia[a] | 14% |
| Sodium Ascorbate | 4% |
| Citric Acid Anhydrous | 0.78% |
| Folded Oil | 0.33% |
| Flavor Masker[b] | 0.2% |
| Rosemary Extracts[c] | 0.2% |
| Mixed Tocopherols[d] | 0.2% |
| Potassium Sorbate | 0.08% |

[a]TICAMULSION ® A-2010 Powder (TIC Gums)
[b]Flavor Masking 599469AH (Firmenich)
[c]Rosemary STABILENHANCE ® OSR 5% 001280 (Naturex Inc.)
[d]TOCOBLEND ® L70 (Vitablend BV)

Example 4

The following emulsions were prepared similarly to the emulsion in Example 3.

TABLE 4

Composition of a final emulsion.

| Ingredient | Percent (w/w) |
|---|---|
| Water | 33% |
| Glycerin | 31.03% |
| Food Starch-Modified[a] | 15% |
| Martek Algal Oil (40% DHA oil) | 10% |
| Citric Acid, Anhydrous | 5.4% |
| Sodium Ascorbate | 2.5% |
| Trisodium Citrate Anhydrous | 2.5% |
| Sodium Hexametaphosphate | 0.15% |
| Flavor Masker[b] | 0.15% |
| Rosemary Extracts[c] | 0.1% |

TABLE 4-continued

Composition of a final emulsion.

| Ingredient | Percent (w/w) |
|---|---|
| Mixed Tocopherols[d] | 0.1% |
| Potassium Sorbate | 0.07% |

[a]Cargill EmulTru ™ 12674
[b]Flavor Masking 599469AH (Firmenich)
[c]Rosemary STABILENHANCE ® OSR 5% 001280 (Naturex Inc.)
[d]TOCOBLEND ® L70 (Vitablend BV)

TABLE 5

Composition of a final emulsion.

| Ingredient | Percent (w/w) |
|---|---|
| Water | 34.23% |
| Glycerin | 30.43% |
| Food Starch-Modified[a] | 0.15% |
| Martek Algal Oil (40% DHA oil) | 10% |
| Citric Acid, Anhydrous | 4.8% |
| Sodium Ascorbate | 2.5% |
| Trisodium Citrate Anhydrous | 2.5% |
| Sodium Hexametaphosphate | 0.15% |
| Flavor Masker[b] | 0.15% |
| Mixed Tocopherols[c] | 0.1% |
| Rosemary Extracts[d] | 0.1% |
| Potassium Sorbate | 0.07% |

[a]National Starch & Chemical (Purity Gum 2000)
[b]Flavor Masking 599469AH (Firmenich)
[c]Tocoblend ® L70 (Vitablend BV)
[d]Rosemary STABILENHANCE ® OSR 5% 001280 (Naturex Inc.)

TABLE 6

Composition of a final emulsion.

| Ingredient | Percent (w/w) |
|---|---|
| Water | 30% |
| Glycerin | 29.03% |
| Modified Gum Acacia[a] | 15% |
| Martek Algal Oil (40% DHA oil) | 15% |
| Citric Acid, Anhydrous | 5.4% |
| Sodium Ascorbate | 2.5% |
| Trisodium Citrate Anhydrous | 2.5% |
| Sodium Hexametaphosphate | 0.15% |
| Flavor Masker[b] | 0.15% |
| Mixed Tocopherols[c] | 0.1% |
| Rosemary Extracts[c] | 0.1% |
| Potassium Sorbate | 0.07% |

[a]TICAMULSION ® A-2010 Powder (TIC Gums)
[b]Flavor Masking 599469AH (Firmenich)
[c]Tocoblend ® L70 (Vitablend BV)
[d]Rosemary STABILENHANCE ® OSR 5% 001280 (Naturex Inc.)

Example 5

The stability of the oil-in-water emulsions prepared in Examples 1 and 3 was tested by maintaining the emulsions at a temperature of −17° C. for a period of 5, 6, 8, or 10 months, followed by thawing the oil-in-water emulsions to a temperature of 4° C. and quantitatively assessing the properties of the emulsions.

The oil-in-water emulsions (10 mL) were placed in a 15 mL vial in an ice cream maker (quick freeze) or a regular freezer (slow freeze) and stored at −17° C. for up to 10 months. The particle size of the oil phase was measured after the designated period at −17° C., and is reported in Tables 4 and 5, below. Particle size was measured using a Malvern Mastersizer Hydro 2000S (Malvern Instruments, Ltd., Worcestershire, UK). Individual samples of the oil-in-water emulsions were removed from the freezer at the designated interval, thawed, and the particle size and organoleptic qualities (using juice model tests) of the emulsions were determined.

TABLE 7

Particle size data as a function of emulsion stability for the oil-in-water emulsions prepared in Example 1.

| Sample Name | d(0.5) | D[4,3] | Uniformity* |
|---|---|---|---|
| Initial at 4° C. | 0.127 | 0.136 | 0.338 |
| Quick Freeze, 5 mths. | 0.129 | 0.137 | 0.305 |
| Slow Freeze, 5 mths. | 0.126 | 0.134 | 0.318 |
| Quick Freeze, 6 mths. | 0.127 | 0.136 | 0.34 |
| Slow Freeze, 6 mths. | 0.127 | 0.136 | 0.34 |
| Quick Freeze, 8 mths. | 0.127 | 0.137 | 0.338 |
| Slow Freeze, 8 mths. | 0.126 | 0.135 | 0.335 |
| Quick Freeze, 10 mths. | 0.122 | 0.132 | 0.373 |
| Slow Freeze, 10 mths. | 0.127 | 0.136 | 0.336 |

*A lower uniformity number corresponds to a higher quality emulsion.

TABLE 8

Particle size data as a function of emulsion stability for the oil-in-water emulsions prepared in Example 3.

| Sample Name | d(0.5) | D[4,3] | Uniformity* |
|---|---|---|---|
| Initial at 4° C. | 0.154 | 0.17 | 0.413 |
| Quick Freeze, 5 mths. | 0.151 | 0.168 | 0.418 |
| Slow Freeze, 5 mths. | 0.148 | 0.169 | 0.472 |
| Quick Freeze, 6 mths. | 0.175 | 0.193 | 0.423 |
| Slow Freeze, 6 mths. | 0.175 | 0.194 | 0.424 |
| Quick Freeze, 8 mths. | 0.168 | 0.186 | 0.421 |
| Slow Freeze, 8 mths. | 0.164 | 0.182 | 0.422 |
| Quick Freeze, 10 mths | 0.164 | 0.182 | 0.42 |
| Slow Freeze, 10 mths. | 0.169 | 0.187 | 0.422 |

*A lower uniformity number corresponds to a higher quality emulsion.

As shown in Tables 7 and 8, the particle size of the oil-in-water emulsions did not change significantly even after 10 months of storage at −17° C.

The organoleptic qualities of the oil-in-water emulsions were determined by an expert panel taste test. Briefly, the emulsions (32 mg DHA) were mixed with 8 oz. white grape or Concord grape juice, microwaved, and tested using an expert panel. The formulations of Examples 1 and 3 had good organoleptic quality.

Example 6

The freeze-thaw stability of the oil-in-water emulsions prepared in Example 4, Table 5, were tested by maintaining the emulsions at a temperature of −17° C. for a period of 5 weeks. Each week the emulsion was thawed to a temperature of 4° C. and tested. The particle size of the oil phase was measured using a Malvern Mastersizer Hydro 2000S (Malvern Instruments, Ltd., Worcestershire, UK) after the designated number of freeze-thaw cycles, and is reported in Table 9, below. The data are represented graphically in FIG. 1.

TABLE 9

Particle size data as a function of emulsion stability for the oil-in-water emulsions prepared in Example 1.

| # Freeze Thaw Cycles | d(0.5) (μm) | D[3,2] (μm) | D[4,3] (μm) | (%)Results 0.01 μm-0.36 μm | Uniformity* |
|---|---|---|---|---|---|
| 0 | 0.122 | 0.115 | 0.129 | 100 | 0.289 |
| 1 | 0.123 | 0.114 | 0.131 | 100 | 0.322 |
| 2 | 0.121 | 0.112 | 0.130 | 100 | 0.330 |
| 3 | 0.120 | 0.111 | 0.130 | 100 | 0.342 |
| 4 | 0.121 | 0.11 | 0.132 | 100 | 0.364 |
| 5 | 0.121 | 0.11 | 0.132 | 100 | 0.364 |

*A lower uniformity number corresponds to a higher quality emulsion.

As shown in Table 9, the oil-in-water emulsion of example 4, table 5, passed 5 freeze-thaw cycles without a change in particle size.

Example 7

The freeze-thaw stability of the oil-in-water emulsions prepared in Example 4, tables 4 and 6, was tested by maintaining the emulsions at a temperature of −17° C. for a period of 5 weeks. For the stability test, the frozen oil-in-water emulsions were thawed overnight once each week to a temperature of 4° C., tested and refrozen.

The oil-in-water emulsions were tested using a "beverage-ring" test. Briefly, 540 g of water, 0.3 g potassium sorbate and 60 g sucrose were added to a beaker and mixed for 2 minutes. Citric acid was added to adjust the pH of the solution to 4.0. An equivalent amount of the emulsion to be tested was added to the beaker while mixing. The mixture was then poured into two Boston round glass bottles. One was placed horizontally and the other vertically. The bottles were monitored for 10 days at room temperature. Rings were identified by gently tipping the solution in the glass bottles and examining for a visible ring at the top of the solution on the interior of the bottle. If no ring forms, the emulsion has passed the ring test. The measurement of the particle size of the oil phase and the ring test were performed after the designated number of freeze-thaw cycles, and is reported in Tables 10 and 11, below.

TABLE 10

Particle size data as a function of freeze-thaw stability for the oil-in-water emulsions prepared in Example 4, Table 4.

| Weeks | D(0.5) (μm) | D[3,2] (μm) | D[4,3] (μm) | (%) Results 0.01 μm-0.36 μm | Uniformity | Ring Test (Pass/Fail) |
|---|---|---|---|---|---|---|
| 0 | 0.120 | 0.113 | 0.128 | 100 | 0.306 | Pass |
| 1 | 0.125 | 0.115 | 0.134 | 100 | 0.338 | Pass |
| 2 | 0.119 | 0.107 | 0.130 | 100 | 0.373 | Pass |
| 3 | 0.119 | 0.107 | 0.130 | 100 | 0.374 | Pass |
| 4 | 0.119 | 0.107 | 0.130 | 100 | 0.373 | Pass |
| 5 | 0.121 | 0107 | 0.130 | 100 | 0.372 | Pass |

TABLE 11

Particle size data as a function of freeze-thaw stability for the oil-in-water emulsions prepared in Example 4, Table 6.

| Weeks | D(0.5) (μm) | D[3,2] (μm) | D[4,3] (μm) | (%) Results 0.01 μm-0.36 μm | Uniformity | Ring Test (Pass/Fail) |
|---|---|---|---|---|---|---|
| 0 | 0.138 | 0.126 | 0.146 | 100 | 0.326 | Pass |
| 2 | 0.141 | 0.129 | 0.148 | 100 | 0.300 | Pass |
| 5 | 0.133 | 0.121 | 0.141 | 100 | 0.329 | Pass |

As shown in Tables 10 and 11, the formulations of Example 4, tables 4 and 6, have consistent particle size and passed the ring test after several freeze-thaw cycles.

Example 8

Sensory Score of a Six Month Emulsion

A descriptive analysis (DA) test was conducted to obtain a sensory score over six months for emulsions made according to the invention as follows. For each preparation, the strength of each attribute was rated on a 0-15 point intensity scale with 0=none and 15=very strong. Martek DA panelists who were trained and experienced in detailed aroma and flavor analysis evaluated the Concord Grape Juice. The compositions that were evaluated were:

The emulsions were prepared using starch obtained from two different starch suppliers (Cargill starch—"CS" (Emul-Tru™ 12674) and National Starch & Chemical—"NS") and one modified gum acacia supplier (TICAMULSION® A-2010 Powder, (TIC Gum—"MGA")) and a chiller temperature of −20° C. A total of three emulsions were prepared as follows:

CS-20: Cargill Starch used as emulsifier;
MGA-20: TIC Gum modified gum acacia used as emulsifier; and
NS-20C: Modified food starch from National Starch & Chemical used as emulsifier.

A score of 2 is the highest passing score. none of emulsions received a sensory score greater than 2 over the six month period of evaluation.

The CS-20, MGA-20 and NS-20C emulsions prepared above as in Table 4 were dosed in Welch's Concord grape juice at 32 mg DHA/250 g juice. The dosed grape juice was processed with a microThermics with a preheat temperature of 250° F. and a filling temperature of 185° F. The treated grape juice was filled in PET bottles and cooled down and stored at room temperature. The following samples were tested:

(1) Control 1 containing grape juice dosed with emulsion prepared by the same formulation as above but in which high oleic sun flower oil (HOSO) replaced DHA™-S oil;
(2) control 2 containing grape juice processed by microThermics without adding any emulsion;
(3) Sample 1 containing grape juice dosed with CS-20C emulsion and processed by microThermics;
(4) Sample 2 containing grape juice dosed with NS-20C emulsion and processed by MicroThermics;
(5) Sample 3 containing grape juice dosed with NS-20C emulsion and processed by microThermics.

The emulsions were assessed for the presence of juice fishy/painty aromatics, under two conditions: (a) storing the sample at 32.2° C. for 16 weeks (which accelerated the development of any aromatics), and (b) storing the sample at room temperature for 3 months. As above, the sensory spectrum DA (descriptive analysis) sensory score is a spectrum 15 point intensity scale in which 0=none and 15=strong intensity. None of the samples accelerated at (stored at) 32.2° C., at the end of 16 weeks, or the samples stored a room temperature, at the end of 3 months, had an intensity scale score greater than 2.

Example 9

Different-From-Control (DFC) Test

A Different-From-Control (DFC) test was conducted as follows. The DFC test was conducted with Martek employees. Panelists were instructed to compare the unfortified sample (control) to all the other variables fortified with DHA, to determine if a difference exists between them. They were also instructed to measure the size of the difference, if any, on the 7 point scale of 0-6, with 0 being no difference was found to 6 being a very large difference was found. There was little or no change in the DFC test results for any of the samples after three months at room temperature.

Example 10

Q-Naturale™-Glycerin Based Thermally Stable Emulsion

To make a Q-Naturale™-glycerin based thermally stable emulsion, the following procedure was used. Q-Naturale™ from National Starch Food Innovation was used. Glycerin was added into the Q-Naturale™ solution using a high shear mixer at 6000 rpm. The dry ingredients (sodium hexametaphosphate, sodium ascorbate, trisodium citrate anhydrous, potassium sorbate and citric acid) were mixed in at 6000 rpm on the high speed mixer. Martek DHA™-S oil and other oil components (flavor masking, rosemary extract, and tocoblend) were mixed in at 6000 rpm on the high shear mixer. The preparation was mixed until all oil was emulsified and did not cling to the edges (1 minute). The emulsion was then homogenized using 10000 psi for the first stage and 1000 psi for the second stage. The product was cooled by applying a cold water bath on the product hose and a circulation water bath on the homogenizer. The first 10 seconds of the products that were produced were discarded. Thirty seconds of cycling time was allowed before collecting next pass products. The products were homogenized for 8 passes. The resulting emulsion was bottled, purged with nitrogen and placed in the freezer. The composition of the final emulsion is shown in Table 12.

TABLE 12

Q-Naturale ™ - Glycerin Emulsion

| Ingredient | Wt % | grams |
|---|---|---|
| Q Naturale ™ 200, 20-22 Brix | 30.00 | 150.00 |
| Glycerin | 29.03 | 145.15 |
| Sodium Hexametaphosphate | 0.15 | 0.75 |
| Sodium Ascorbate | 2.50 | 12.50 |
| Trisodium Citrate Anhydrous | 2.50 | 12.50 |
| Potassium Sorbate | 0.07 | 0.35 |
| Citric Acid, anhydrous | 5.40 | 27.00 |
| Martek DHA ™-S Rosemary Sun | 30.00 | 150.00 |
| Flavor Masking 599469AH (from Firmiech) | 0.15 | 0.75 |
| Rosemary STABILENHANCE ® OSR 5% 001280 | 0.10 | 0.50 |
| Tocoblend ™ 70 IP | 0.10 | 0.50 |
| Total | 100.00 | 500.00 |

Martek DHA™-S Rosemary Sun is a rosemary extract that contains sunflower lecithin Q-Naturale™ is a natural oil emulsifier derived from the quillaja tree and is available commercially from National Starch Food Innovation. It is a molecule that performed similarly to gum arabic (gum acacia) in sensory evaluations and creates emulsions with similar opacity levels to those of gum arabic and starch. It is stable in a wider range of pH and temperature however.

The particle size of the freezable emulsion produced above was tested for the uniformity and size of the particles initially after preparation and three months after storage. The results are shown in Table 13.

TABLE 13

| Uniformity | | Median (µm) | | % 0.36-5 µm | | % 0.01-0.36 µm | |
|---|---|---|---|---|---|---|---|
| 0 month | 3 months | 0 month | 3 months | 0 month | 3 months | 0 month | 3 months |
| 0.262 | 0.262 | 0.112 | 0.112 | 0 | 0 | 100 | 100 |

The emulsion scored a passing score when subject to the Ring Test. A Hot Fill Test was conducted with 150° F. preheat/200° F. final heat/175° F. filling temperature. The emulsion was dosed in Welch's grape juice. The dosing level of the emulsion was 32 mg DNA/250 g. No creaming was found as a result of the "Hot Fill Test."

Example 11

Formulation of a Modified Starch Based Thermally Stable Emulsion with Propylene Glycol A modified starch based thermally stable emulsion with propylene glycol was prepared as shown in Table 14.

TABLE 14

Modified starch and propylene glycol

| Ingredient | Wt % | grams |
|---|---|---|
| Cargill EmulTru ™ 12674 starch | 15.00 | 75 |
| Propylene Glycol | 31.03 | 155.15 |

TABLE 14-continued

Modified starch and propylene glycol

| Ingredient | Wt % | grams |
|---|---|---|
| Sodium Hexametaphosphate | 0.15 | 0.75 |
| Sodium Ascorbate | 2.50 | 12.50 |
| Trisodium Citrate Anhydrous | 2.50 | 12.50 |
| Potassium Sorbate | 0.07 | 0.35 |
| Citric Acid, anhydrous | 5.40 | 27.00 |
| DHA S Rosemary Sun | 10.00 | 50.00 |
| Flavor Masking 599469AH | 0.15 | 0.75 |
| Rosemary STABILENHANCE ® OSR 5% 001280 | 0.10 | 0.50 |
| Tocoblend ™ 70 IP | 0.10 | 0.50 |
| Water (deionized) | 33.00 | 165 |
| Total | 100.00 | 500.00 |

Example 12

Formulation of a Modified Starch Based Thermally Stable Emulsion with Propylene Glycol, Triacetin and Glycerin A modified starch based thermally stable emulsion with propylene glycol, triacetin and glycerin was prepared as shown in Table 15

TABLE 15

Modified starch, propylene glycol triacetin and glycerin

| Ingredient | Wt % | grams |
|---|---|---|
| Cargill EmulTru ™ 12674 starch | 15.00 | 75 |
| Glycerin | 4.00 | 20 |
| Propylene Glycol | 14.03 | 70.15 |
| Triacetin | 13.00 | 65 |
| Sodium Hexametaphosphate | 0.15 | 0.75 |
| Sodium Ascorbate | 2.50 | 12.50 |
| Trisodium Citrate Anhydrous | 2.50 | 12.50 |
| Potassium Sorbate | 0.07 | 0.35 |
| Citric Acid, anhydrous | 5.40 | 27.00 |
| DHA S Rosemary Sun | 10.00 | 50.00 |
| Flavor Masking 599469AH | 0.15 | 0.75 |
| Rosemary STABILENHANCE ® OSR 5% 001280 | 0.10 | 0.50 |
| Tocoblend ™ 70 IP | 0.10 | 0.50 |
| Water (deionized) | 33.00 | 165 |
| Total | 100.00 | 500.00 |

CONCLUSION

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A thermally stable oil-in-water emulsion comprising:
an oil comprising a polyunsaturated fatty acid,
water,
an emulsifier, and
a water-soluble stabilizer, wherein
the water-soluble stabilizer consists of a mixture of sodium chloride in a concentration of about 10% to 25% by weight of the emulsion, and a monosaccharide in a concentration of about 3% to 15% by weight of the emulsion, and wherein
the thermally stable oil-in-water emulsion is flowable at a temperature of −40° C., and is free from a variation in particle size after 9 months in storage at a temperature of −40° C. to −15° C.

2. The emulsion of claim 1, wherein the emulsion is flowable at a temperature of −80° C.

3. The emulsion of claim 1, wherein the thermally stable oil-in-water emulsion is free from a variation in particle size after 10 freeze-thaw cycles.

4. The emulsion of claim 1, further comprising propylene glycol in a concentration of 10% to 30% by weight of the emulsion.

5. The emulsion of claim 1, further comprising glycerol in a concentration of 25% to 46% by weight of the emulsion.

6. The emulsion of claim 1, wherein the polyunsaturated fatty acid is at least one selected from the group consisting of α-linolenic acid, γ-linolenic acid, linoleic acid, conjugated linoleic acid, arachidonic acid, ω-3 docosapentaenoic acid, ω-6 docosapentaenoic acid, eicosapentaenoic acid, docosahexaenoic acid, and oxylipins.

7. The emulsion of claim 1, wherein the polyunsaturated fatty acid is present in a concentration of 5% to 40% by weight of the emulsion.

8. The emulsion of claim 1, wherein the emulsifier is present in a concentration of 10% to 30% by weight of the emulsion.

9. The emulsion of claim 1, wherein the emulsifier is at least one selected from the group consisting of a modified gum acacia, a lecithin, an agar, a modified ghatti gum, a pectin, a carrageenan, a xanthan gum, a modified food starch, a modified alginate, a polyoxyethylene sorbitan ester, and a sugar ester.

10. The emulsion of claim 1, wherein the water is present in a concentration of 20% to 60% by weight of the emulsion.

11. A thermally stable oil-in-water emulsion comprising:
an oil comprising a polyunsaturated fatty acid in a concentration of 5% to 40% by weight,
water in a concentration of 20% to 60% by weight,
modified starch as an emulsifier, and
a water-soluble stabilizer consisting of sodium chloride in a concentration of 10% to 25% by weight and a monosaccharide in a concentration of 3% to 15% by weight, wherein
the thermally stable oil-in-water emulsion remains flowable at a temperature of −40° C., and is free from a variation in particle size after 9 months in storage at a temperature of −40° C. to −15° C.

12. The emulsion of claim 11, wherein the emulsion is flowable at a temperature of −80° C.

13. The emulsion of claim 1, wherein the emulsion has a pH of 2 to 7.

14. The emulsion of claim 1, further comprising a taste-masking agent.

15. The emulsion of claim 1, further comprising a preservative.

16. The emulsion of claim 1, further comprising an antioxidant.

17. The emulsion of claim 16, wherein the antioxidant is at least one selected from the group consisting of vitamin C, vitamin E, a polyphenol, a phenol derivative, carnosic acid, lipoic acid, taurine, and an aromatic carboxylic acid.

18. A process for preparing a thermally stable oil-in-water emulsion, the process comprising:
- combining water and an emulsifier to provide an aqueous mixture,
- adding to the aqueous mixture an oil comprising a polyunsaturated fatty acid while mixing to provide a oil-in-water emulsion, and
- adding to the oil-in-water emulsion a water-soluble stabilizer consisting of a mixture of sodium chloride in a concentration of about 10% to 25% by weight of the emulsion, and a monosaccharide in a concentration of about 3% to 15% by weight of the emulsion to provide a thermally stable oil-in-water emulsion,
- wherein the thermally stable oil-in-water emulsion remains flowable at a temperature of −40° C., and is free from a variation in particle size after 9 months in storage at a temperature of −40° C. to −15° C.

19. The process of claim 18, wherein the emulsion is flowable at a temperature of −80° C.

\* \* \* \* \*